US009228219B2

(12) United States Patent
De Roos et al.

(10) Patent No.: US 9,228,219 B2
(45) Date of Patent: Jan. 5, 2016

(54) METHODS OF TREATMENT USING WATER-SOLUBLE TRYPTOPHAN-CONTAINING PEPTIDES OBTAINED BY THE HYDROLYSIS OF HENS EGGS LYSOZYME

(71) Applicant: DSM IP Assets B.V., Heerlen (NL)

(72) Inventors: Andre Leonardus De Roos, Delft (NL); Luppo Edens, Rotterdam (NL); Rudolf Franciscus Van Beckhoven, Bavel (NL); Alexander Lucia Leonardus Duchateau, Lanaken (BE); Joris Kloek, Gouda (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/694,103

(22) Filed: Oct. 31, 2012

(65) Prior Publication Data

US 2013/0231278 A1 Sep. 5, 2013

Related U.S. Application Data

(63) Continuation of application No. 12/447,332, filed as application No. PCT/EP2007/061701 on Oct. 30, 2007, now abandoned.

(30) Foreign Application Priority Data

| Nov. 2, 2006 | (EP) | 06123358 |
| Jan. 18, 2007 | (EP) | 07100755 |
| Sep. 3, 2007 | (EP) | 07115528 |

(51) Int. Cl.

| *C12P 21/06* | (2006.01) |
| *C12P 13/22* | (2006.01) |
| *A23K 1/16* | (2006.01) |
| *A23L 1/305* | (2006.01) |
| *A61K 38/05* | (2006.01) |
| *A61K 38/06* | (2006.01) |

(52) U.S. Cl.
CPC .............. *C12P 21/06* (2013.01); *A23K 1/1631* (2013.01); *A23L 1/3053* (2013.01); *A61K 38/05* (2013.01); *A61K 38/06* (2013.01); *C12P 13/22* (2013.01)

(58) Field of Classification Search
None
See application file for complete search history.

(56) References Cited

U.S. PATENT DOCUMENTS

2004/0058866 A1* 3/2004 Mallee et al. .................. 514/12

FOREIGN PATENT DOCUMENTS

| EP | 1757289 | 2/2007 |
| WO | WO 02/46210 | 6/2002 |
| WO | WO 2005/102321 | 11/2005 |
| WO | WO 2006/009448 | 1/2006 |

OTHER PUBLICATIONS

Ferguson, Prim Care Companion J Clin Psychiatry. Oct. 2000; 2(5): 173-178; downloaded Mar. 24, 2014 from ncbi.nlm.nih.gov/pmc/articles/PMC181135; 7 pages total.*
Polypeptide information downloaded on Apr. 22, 2012 from: ncbi.nlm.nih.gov/protein/BAC06860.1; copied and pasted directly into the Office action (Appendix I).*
Vickers, Drugs Aging, 2002, 19(7): 487-494.*
Andrews et al., Neuroscience and Biobehavioral Reviews, 2015; 51: 164-188.*
Hulsken et al., Nutrition Research Reviews, 2013; 26: 223-234.*
Khaliq et al., Pak. J. Pharm. Sci., 2006; 19:11-15.*
International Search Report for PCT/EP2007/061701, mailed Jan. 31, 2008.
Mine et al., "Antimicrobial Peptides Released by Enzymatic Hydrolysis of Hen Egg White Lysozyme", Journal of Agricultural and Food Chemistry, vol. 52, (2004), pp. 1088-1094.
Hunter, Howard N., et al., "The Interactions of Antimicrobial Peptides Derived from Lysozyme with Model Membrane Systems", Biochimica et Biophysica Acta, vol. 1668, (2005), pp. 175-189.
Beulens, Joline W.J. et al., "Alpha-lactalbumin Combined with a Regular Diet Increases Plasma Trp-LNAA Ratio", Physiology & Behaviour, vol. 81, (2004), pp. 585-593.
Hermann, Jacques et al., "Multiple Forms of Duck-Egg-White Lysozyme", European Journal of Biochemistry, vol. 24, (1971), pp. 12-17.
Nishio et al., "Digestion of Protein Substrates by Subtilisin: Immobilization Changes the Pattern of Products", Archives of Biochemistry and Biophysics, vol. 229, (1984), pp. 304-311.
Markus et al, "Effect of different tryptophan sources on amino acid availability to the brain and mood in healthy volunteers", Psychopharmacology 201:107-114 (2008).
Markus et al, "Effect of tryptophan-rich egg protein hydrolysate on brain ryptophan availability, stress and performance", Clinical Nutrition 29:610-616 (2010).
Markus et al, "Evening intake of α-lactalbumin increases plasma tryptophan availability and improves morning alertness and brain measures of attention", Am. J. Clin. Nutr. 81:1026-1033 (2005).

* cited by examiner

*Primary Examiner* — Christina Borgeest
(74) *Attorney, Agent, or Firm* — Nixon & Vanderhye P.C.

(57) ABSTRACT

The present invention relates to a process to produce a composition comprising water-soluble peptides and having a Trp/LNAA ratio of more than 0.15, which comprises hydrolyzing lysozyme, preferably hen eggs lysozyme, to prepare a hydrolysate having a DH of between 5 and 45.

5 Claims, 8 Drawing Sheets

Figure 1:
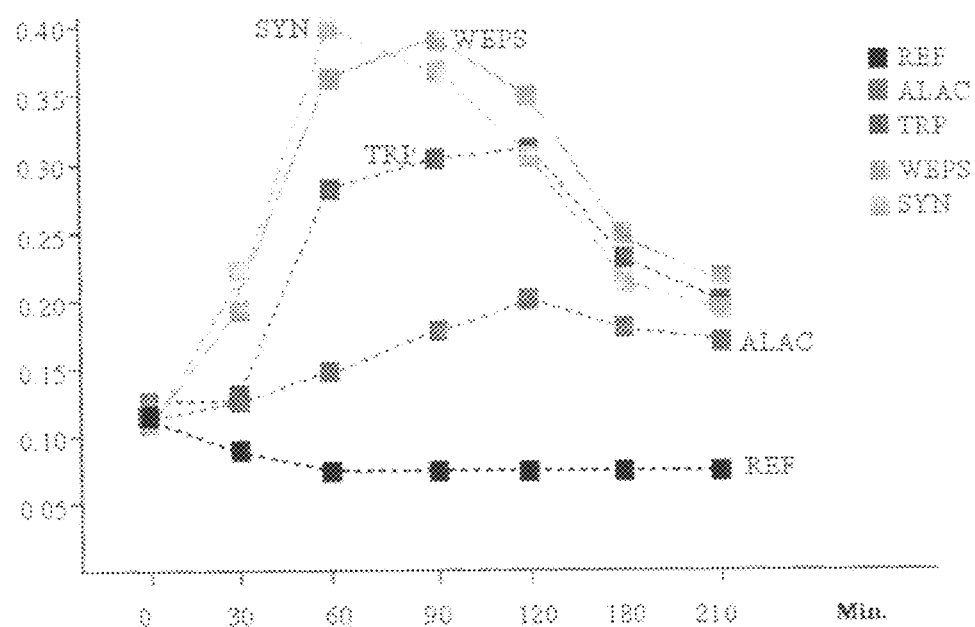

METHODS OF TREATMENT USING WATER-SOLUBLE TRYPTOPHAN-CONTAINING PEPTIDES OBTAINED BY THE HYDROLYSIS OF HENS EGGS LYSOZYME

This application is a continuation of U.S. application Ser. No. 12/447,332, filed 12 Nov. 2009 (abandoned), which is the U.S. national phase of International Application No. PCT/EP2007/061701 filed 30 Oct. 2007, which designated the U.S. and claims priority to EP Application No. 06123358.1, filed 2 Nov. 2006; EP Application No. 07100755.3, filed 18 Jan. 2007; and EP Application No. 07115528.7, filed 3 Sep. 2007, the entire contents of each of which are hereby incorporated by reference.

FIELD OF THE INVENTION

The present invention relates to peptides comprising tryptophan residues.

BACKGROUND OF THE INVENTION

Serotonine levels in the brain have been linked with mood, alertness, vigilance, sleep onset and quality, anxiolytic effects, depression, affective reaction control, appetite and sexual behavior. Many publications exist in which changes in brain serotonin levels are correlated with the availability of the natural amino acid L-tryptophan (Trp or W). Because of this correlation, methods to increase plasma tryptophan levels have received a lot of attention. Tryptophan quantities of around 1 gram/day per individual have been reported to yield clinically significant effects (Markus et al., Am. J. Clin. Nutr 2005; 81, 1026-1033). One method to increase plasma tryptophan levels involves the consumption of protein preparations enriched in the whey protein alpha-lactalbumin. Alpha-lactalbumin preparations are readily available and have a relatively high tryptophan concentration. However, approaches in which the alpha-lactalbumine is provided as such, see for example DE 4130284 and JP 2279700, do not take into account that the main determinant of brain tryptophan and serotonin levels is not plasma tryptophan concentration alone, but the socalled Trp/LNAA ratio (Femstrom and Wurtman. Science 1971, 173, 149-152). This Trp/LNAA ratio represents the molar ratio of tryptophan relative to the levels of Large Neutral Amino Acids (LNAA: i.e. the sum of tyrosine, phenylalanine, leucine, isoleucine and valine) in plasma. These LNAA compete with tryptophan for uptake into the brain, presumably because the same transport mechanism across the blood-brain barrier is used. Therefore, the most effective way of increasing brain tryptophan concentrations is to supply preparations with a high Trp/LNAA ratio. A number of publications a.o. WO 02/46210, refer to the preparation of peptide fractions from alpha-lactalbumin having improved Trp/LNAA ratio's.

Obviously the use of free tryptophan, i.e. the free amino acid, would provide the simplest and cheapest approach to provide preparations with a high Trp/LNAA ratio. However, in many countries legislation exists that tightly regulates the supply of free tryptophan. The maximal allowable free tryptophan levels in its various application forms vary per country. To supply additional dietary tryptophan in a more natural way, more recent approaches aim at providing tryptophan rich proteins. As mentioned, alpha-lactalbumin as well as its hydrolysates have gained popularity as a safe option to enhance plasma tryptophan levels. However, the use of alpha-lactalbumin as a starting point for tryptophan-rich preparations, comes with disadvantages in terms of maximal Trp/LNAA ratios and costs. Alpha-lactalbumin and beta-lactoglobulin form the major protein constituents of whey. Because on an industrial scale a complete separation of alpha-lactalbumin and beta-lactoglobulin is difficult, the implication is that cost effective alpha-lactalbumin preparations will contain beta-lactoglobulin as well. Whereas alpha-lactalbumin has a molar tryptophan content of 5.3%, the tryptophan content of beta-lactoglobulin is only 2%. Whereas alpha-lactalbumine has a molar Trp/LNAA ratio of 0.11, beta-lactoglobulin has a molar Trp/LNAA ratio of not more than 0.04. So obviously any contamination of the alpha-lactalbumin preparation with beta-lactoglobulin, will dramatically lower the Trp/LNAA ratio of the final product.

In view of the broad interest in preparations that can modulate brain serotonine levels, there is a need for improved production methods for protein and peptide preparations having a high Trp/LNAA ratio that are broadly applicable in various food and neutraceutical products.

BRIEF DESCRIPTION OF THE INVENTION

The present invention relates to a process to produce a composition comprising a water-soluble, tryptophan-containing peptide, preferably at least two water-soluble, tryptophan-containing peptides, and having a Trp/LNAA ratio of more than 0.15, preferably between 0.15 and 1.8, which comprises hydrolyzing lysozyme, preferably hen eggs lysozyme, to prepare a hydrolysate having a DH of between 5 and 45, and optionally removing part of the arginine or lysine containing peptides. Preferably the composition comprises AW or GNW, more preferably AW and GNW. The hydrolysate has preferably a DH between 10 and 40.

The present invention also relates to a composition comprising at least two different water-soluble peptides and wherein the molar Trp/LNAA ratio of the composition is at least 0.15, preferably between 0.15 and 1.8. Preferably this composition comprises AW or GNW, preferably AW and GNW and most preferably AW and GNW whereby the molar ratio of AW to GNW is between 1 to 2 and 10 to 1, preferably between 1 to 2 and 5 to 1. Moreover the present invention provides a composition of water-soluble peptides which are rich in tryptophan. Advantageously, the present invention further relates to a composition comprising at least two different di- or tripeptides, whereby two peptides selected from di- or tripeptides are present in an amount of at least 5 mol % of the total amount of di- and tripeptides, and in which composition more than 30 mol %, preferably more than 40 mol %, more preferably more than 50 mol %, even more preferably more than 60 mol %, still more preferably more than 70 mol % and most preferably more than 80 mol % of the peptide-bound tryptophan is present in the form of a di- or a tripeptide, preferably the composition has a Trp/LNAA ratio of more than 0.15, preferably between 0.15 and 1.8. By peptide-bound tryptophan is meant a tryptophan which is present as amino acid in a peptide.

This composition is preferably a lysozyme hydrolysate or a purified lysozyme hydrolysate. In one embodiment of the invention, the lysozyme hydrolysate is particularly rich in arginine residues. Arginine does not belong to the group large, neutral amino acids (LNAA's) but is known for its insulin stimulating effect. We have found that the hydrolysate according to the invention can generate in vivo high blood plasma Trp/LNAA ratios. Quite surprisingly the Trp/LNAA ratios detected in blood plasma, were found to be higher than the Trp/LNAA ratio of the hydrolysate. Yet another advantage of the invention is that the Trp containing peptides are very small so that even in combination with protein-rich products with less favorable Trp/LNAA ratios, the hydrolysate can immediately generate high blood plasma Trp/LNAA ratios. The composition may further comprise free tryptophan. Preferably the hydrolysate does not contain more than 1 wt % (on dry matter) of free tryptophan.

Another aspect of the invention is the use of a composition which is obtained by hydrolyzing lysozyme, preferably hen egg lysozyme, or another composition according to the invention for improving mood, cognition, appetite, alertness, vigilance, sleep onset and quality, anxiolytic effects, depression, affective reaction control or sexual behavior, or for use as ingredient in the preparation of a food, pet food, feed, dietary supplement or neutraceutical composition for mood, cognition, appetite, alertness, vigilance, sleep onset and quality, anxiolytic effects, depression, affective reaction control or sexual behavior. Apart from the lysozyme hydrolysate, the composition may also comprise carbohydrates as well as compounds recommended for "brain" nutrition, for relieving stress or depression or for improving alertness, mood, cognition or sleep patterns. Moreover the present invention relates to the use of AW, SW or GNW for improving mood, cognition, appetite, alertness, vigilance, sleep onset and quality, anxiolytic effects, depression, affective reaction control or sexual behavior, or for use as ingredient in the preparation of a food, feed, dietary supplement or neutraceutical composition for mood, appetite, alertness, sleep onset and quality, anxiolytic effects, depression, affective reaction control or sexual behavior.

A food (including infant formula), pet food, feed, dietary supplement or neutraceutical composition is disclosed comprising the composition produced according to the process of the invention or the composition according according to the invention including GNW, SW or AW as peptides present.

According to a further embodiment the use of water-soluble tryptophan-containing peptides or a composition of the invention for increasing the Trp/LNAA ratio in plasma within 90 minutes, preferably 60 minutes, most preferably 30 minutes after uptake of the peptides or the composition, or for the preparation of a neutraceutical composition for increasing the Trp/LNAA ratio in plasma within 90 minutes, preferably 60 minutes, most preferably 30 minutes after uptake of the peptides.

DETAILED DESCRIPTION OF THE INVENTION

The present invention provides a composition comprising tryptophan present in peptide form which is very suitable for giving an effective increase of the Trp/LNAA ratio in plasma in a very short time interval. We noted that di- and tripeptides comprising tryptophan advantageously contribute to this increase. In one embodiment of the present invention, lysozyme, preferably hen egg lysozyme is enzymatically (pre-)hydrolysed in an industrial process i.e. (hen egg) lysozyme is preferably provided in the form of a hydrolysate. Offered in the form of a hydrolysate, the gastro-intestinal absorbtion of tryptophan containing peptides is greatly facilitated. In another embodiment of the present application, hen egg lysozyme is converted into a hydrolysate in which the levels of peptides comprising the positively charged arginine and lysine residues have been lowered. The latter hydrolysates are characterized by molecular Trp/LNAA ratios higher than 0.15. In yet another embodiment of the present application, hen egg lysozyme is converted to a hydrolysate comprising a peptide population of which more than 50%, preferably more than 60%, more preferably more than 75% of the peptides present have a molecular weight below 500 Da. This with the proviso that the molecular weight distribution of the peptides present in the hydrolysate is carried out as described in the Materials & Methods section of the present application.

An important advantage of the latter embodiment is that the tryptophan encompassed in di- and tripeptides is transported across the intestine wall into the blood stream immediately after oral consumption. As a consequence, plasma tryptophan levels are increased almost instantaneously with a direct effect on brain serotonin levels. Data presented in Example 6 of the present application show that the tryptophan residues presented in the form of such di- and tripeptides very quickly lead to high Trp/LNAA ratios. In this respect, the tryptophan residues presented in the form of these di- and tripeptides seem to be even more efficacious than free tryptophan. According to the present process a water-soluble peptide fraction is obtained having a molecular Trp/LNAA ratio of at least 0.15 provided that the amino acid analysis of the hydrolysate is carried out as described in the Materials & Methods section of the present application. Yet another important advantage of offering tryptophan in the form of di- and tri-peptides is that the gastro-intestinal uptake of these peptides is so fast, that they can be consumed in combination with protein containing foods, such as dairy products that naturally have a less favorable Trp/LNAA ratio, and yet lead to an effective increase of the Trp/LNAA ratio in the plasma within 90 minutes, preferably 60 minutes, more preferably 30 minutes period after consumption.

Therefore the present invention provides the use of the composition of the invention, for example the water-soluble peptides comprising tryptophan, for the use of obtaining an increased Trp/LNAA ratio in plasma within 90 minutes, preferably 60 minutes, most preferably 30 minutes after uptake of the peptides or for the preparation of a neutraceutical composition for obtaining an increased Trp/LNAA ratio in plasma within 90 minutes, preferably 60 minutes, most preferably 30 minutes after uptake of the peptides. Preferably the consumption of protein or protein-containing food is at the same time or almost the same time as the water-soluble peptides. Increased Trp/LNAA ratio means an increase of this ratio compared to the situation prior to the consumption or uptake of the composition of the invention.

A "protein" or "polypeptide" is defined herein as a chain comprising more than 30 amino acid residues.

A "peptide" or "oligopeptide" is defined herein as a chain of at least two amino acids that are linked through peptide bonds. The terms "peptide" and "oligopeptide" are considered synonymous (as is commonly recognized) and each term can be used interchangeably as the context requires.

A "water-soluble" peptide is a peptide which is soluble in water at a pH of 5.0.

All (oligo)peptide and polypeptide formulas or sequences herein are written from left to right in the direction from amino-terminus to carboxy-terminus, in accordance with common practice. The one-letter code of amino acids used herein is commonly known in the art and can be found in Sambrook, et al. (Molecular Cloning: A Laboratory Manual, $2^{nd}$ ed. Cold Spring Harbor Laboratory, Cold Spring Harbor Laboratory Press, Cold Spring Harbor, N.Y., 1989).

By protein hydrolysate, hydrolysate or hydrolysed protein is meant the product that is formed by enzymatic hydrolysis of the protein, an enriched hydrolysate being a fraction of the protein hydrolysate for example enriched in selected peptides or wherein peptides or polypeptides have been removed from the hydrolysate. So an enriched hydrolysate is preferably a mixture of peptides (or a peptide mixture). The peptide mixture of the invention is therefore a mixture of at least two, preferably at least three, more preferably at least four tryptophan containing peptides. More preferably the mixture comprises a peptide population of which more than 50%, preferably even more than 60%, and most preferably more than 75% of the peptides present have a molecular weight below 500 Da. A tryphophan containing peptide means a peptide which comprises at least one L-tryphophan amino acid residue.

The Trp/LNAA ratio represents the molar ratio of tryptophan relative to the levels of other Large Neutral Amino Acids (LNAA: i.e. the sum of tyrosine, phenylalanine, leucine, isoleucine and valine). Except for the plasma Trp/LNAA ratio, the Trp/LNAA ratio relates only to peptide-bound amino acids. Thus free tryptophan, tyrosine, phenylalanine, leucine, isoleucine and valine are not taken into account in the Trp/LNAA ratio. Peptide-bound amino acids are amino acids which are part of a peptide and not free amino acids.

The Tyr/BCAA ratio represents the molar ratio of tyrosine relative to the levels of branched chain amino acids (BCAA; i.e. the sum of leucine, isoleucine and valine). Preferably the Tyr/BCAA ratio is higher than 0.1, preferably higher than 0.12.

A favourable sleep onset and quality is defined as a quiet sleep entered into within 45 minutes after going to bed.

Mood is defined as the emotional state of mind and preferably measured using the Profile of Mood States questionnaire (see Example 6 of the present application). Cognition is defined as the combined skills relating to such areas as problem solving, learning, memory and language.

Appetite is defined as the desire to eat, stimulated by feelings of hunger.

Alertness is defined as the attentive or vigilant state of mind, preferably measured using the Mackworth Clock Test and Critical Tracking Task (see Example 9 of the present application).

Anxiolytic effects are effects that result in relieving feelings of fear, apprehension or worry.

Depression is defined as a state of mind characterized by severe and persistant feelings of loss of pleasure.

The term sexual behavior is used herein as a synonym for libido.

In WO02/46210 a method for increasing the level of tryptophan in whey protein hydrolysates is described. In the method used, whey is first hydrolysed at acidic pH by one or more acid proteases, preferably by a pepsin, rennin, acid fungal protease, chymosin, papain, bromelain, chymopapain or ficin. The preferred incubation conditions are between pH 1.5 and 3.5 and were chosen to generate peptides having a hydrophobic nature. The hydrolysis is deliberately carried out in such a way that the tryptophan residues become incorporated in large, hydrophobic peptides. Much less tryptophan residues are present in the small, more water soluble peptides. In a subsequent processing step, the pH is raised to 4.0 to 6.0 to promote precipitation of these large, tryptophan-containing, peptides, hereby facilitating their selective recovery from the whey hydrolysate. However, the process as described has several drawbacks. Tryptophan is obtained as present in large, acid-insoluble peptides which implies that application in, for example, acid, drinks will be problematic. Moreover to the fact that tryptophan is present in relatively large peptides, the tryptophan uptake into the blood will be retarded hereby limiting the application possibilities of the preparation as a food or beverage ingredient, especially in combination with othetr proteins. Another disadvantage of the use of such large peptides is that such peptides may give rise to allergic reactions. Such reactions to whey proteins are well known.

The present invention overcomes these disadvantages by disclosing a simple hydrolysis process, starting with a protein that is industrially available and is characterised by a high Trp/LNAA ratio, The present process has a tryptophan yield of more than 30% on protein tryptophan basis and generates a water soluble peptide composition comprising tryptophan. The fact that the larger part of the tryptophan residues is encompassed in di- and tripeptides, implies an immediate uptake into the blood stream. As will be disclosed, this property allows the incorporation of the hydrolysate in a larger variety of food or neutraceutical products. Quite surprisingly the present invention also discloses that upon oral consumption, the hydrolysate according to the invention can generate higher blood plasma Trp/LNAA ratios than the Trp/LNAA ratio of the actual hydrolysate. Finally, the tryptophan-containing peptide mixture is also characterized by a very low antigenicity.

According to the present invention hen egg lysozyme is used as a convenient substrate for providing preparations with a high Trp/LNAA ratio. Lysozyme is present in egg white in a concentration of 3-4%. By taking advantage of its exceptionally high isoelectric point, lysozyme is industrially isolated from egg white using a simple cation chromatographic purification step. The resulting product is almost pure and this industrially available product has a molecular tryptophan content of 7.8% and molecular Trp/LNAA ratio of at least 0.15. Thus, pure lysozyme has a Trp/LNAA ratio that is significantly higher than pure alpha-lactalbumin and or beta-lactoglobulin. Therefore, the lysozyme hydrolysates according to the present invention has preferably a molar Trp/LNAA ratio which is higher than 0.15, more preferably the Trp/LNAA ratio is higher than 0.20, even more preferably the Trp/LNAA ratio is higher than 0.23, still more preferably the Trp/LNAA ratio is higher than 0.25 and most preferably the Trp/LNAA ratio is higher than 0.30. In general the molar Trp/LNAA ratio is below 3.0. As such lysozyme presents a preferred starting point for tryptophan containing peptides or compositions. Lysozyme (EC3.2.1.17) is an enzyme able to hydrolyse specific peptidoglycan bonds in bacterial cell walls leading to cell lysis. Because of its bactericidal effect, lysozyme plays an important role in host defence by preventing infections. Under physiological conditions, the lysozyme molecule is very resistant to proteolytic attack. This unusual resistancy can be explained on evolutionary grounds: as invading bacteria are able to excrete a large variety of proteases, a lysozyme molecule susceptible to such proteases would be rapidly inactivated. Its protease resistance has been illustrated for a.o. stomach lysozymes of ruminants (Dobson et al, J. Biol. Chem. 1984, 259 (18)11607-11616). From a structural point of view, the presence of four disulphide bonds in the molecule can be expected to add to the protease resistancy of lysozyme. On the basis of data presented in Example 1 of the present application, hen egg lysozyme can be considered so resistant to proteolytic attack, that it is unlikely that the molecule can be eficiently digested in the relevant part of the human intestinal tract. The consequence of this protease resistancy is that, despite its very attractive Trp/LNAA ratio, intact lysozyme is not a suitable source for raising plasma tryptophan levels simply because the tryptophan residues are not liberated under the physiological conditions existing in the gastro-intestinal tract.

Upon dietary intake, proteins present in food are gradually hydrolysed to smaller fragments and then transported across the wall of the small intestine and taken up into the blood. In the gastro-intestinal tract a number of different proteases that originate in the stomach, pancreas and small intestine are active to hydrolyse dietary proteins. Endoproteases such as pepsin, trypsin and chymotrypsin cleave large molecular weight proteins into smaller oligopeptides. These oligopeptides are then further hydrolysed by a number of other enzymes such as di- and tripeptidyl peptidases to yield di- and tripeptides and by amino- and carboxypeptidases to yield free amino acids. Carrier systems specific for the transport of free amino acids or di- and tripeptides are responsible for an efficient transport across the intestine wall into the blood stream. Upon dietary intake, free amino acids, di- and tripeptides become immediately incorporated in the blood stream. Peptides larger than tripeptides require additional enzymatic cleavage to enable uptake.

We have found that the hydrolysate according to the invention is also effective if incorporated into high protein containing food matrices as presented by, for example, dairy products. This is quite surprising as protein containing food matrices represent high LNAA loads and thus can be expected to reduce the effect of products with high Trp/LNAA ratios. A possible explanation for this unexpected phenomenon is that the usual food products incorporate intact, rather than extensively hydrolyzed proteins. A typical size distribution of a hydrolysate according to the invention is presented in FIG. 3. According to this Figure, the majority of the tryptophan and tyrosine incorporating peptides has a molecular weight below 500 Da. In view of the very high molecular weight of tryptophan (MW=186) and tyrosine (MW=163) and the fact that only very low levels of free tryptophan are present, the implication is that the majority of these peptides will be tri- or di-peptides. As tryptophane has a much higher molar absorptivity than tyrosine at the wavelength used, peak values will refer to tryptophan incorporating peptides mainly.

Because the tryptophan containing di- and tripeptides according to the invention are absorbed so much faster than, for example, the large quantity of LNAA's presented by non-hydrolyzed matrix proteins, we assume that this is the reason that even in the presence of large quantities of matrix proteins, high plasma Trp/LNAA ratios can be obtained. Such an explanation is particularly relevant for food matrices incorporating caseins and cereal proteins because such proteins exhibit a poor solubility under the acid conditions of the stomach. However, it also applies to matrices incorporating more soluble intact proteins such as whey proteins, because even the gastro-intestinal digestion of such proteins is relatively slow so that the incorporation of the resulting peptides is also significantly delayed in comparison with the tryptophan containing di- and tripeptides according to the invention. According to the data presented in Example 6, such a delay is between 30 and 60 minutes: long enough to absorp all tryptophan containing di- and tripeptides. Therefore the uptake of protein or protein-containing food can be at the same time or almost the same time as the water-soluble peptides. Almost at the same time means that uptake of the peptides is within 60 minutes, preferably 30 minutes after the uptake of the protein.

Interestingly, our present experimental data also seem to indicate that the hydrolysate according to the invention can generate Trp/LNAA ratios in the blood of human volunteers that are higher than the Trp/LNAA ratio of the hydrolysate. Although such a phenomenon is unknown and there exists, according to our best knowledge, no accepted explanation for this effect, we believe that this may be caused by the extremely high arginine content of the lysozyme molecule. The presently posed working hypothesis is disclosed herein to explain the experimental data shown in the Examples. This hypothesis is used to give the present insight of the inventors but the present invention is no way linked or limited to this hypothesis. So the present invention stands independent of the correctness of the hypothesis. An increase in blood insulin stimulates the uptake of amino acids from blood into peripheral tissue, especially muscle. However, tryptophan largely escapes this route due to the fact that in blood, tryptophan is bound to the plasma protein albumin. As a consequence, increased insulin levels decrease the concentrations of LNAA, but not tryptophan, thus increasing the Trp/LNAA ratio in blood. Since carbohydrate ingestion elicits insulin secretion and stimulates the uptake of LNAA in periferal tissues and notably muscles, plasma Trp/LNAA ratio's are increased by carbohydrate intake (Fernstrom and Wurtman, 1972, Metabolism, Vol. 21, No. 4, 337-342). Apart from carbohydrate ingestion, insulin secretion is also known to be stimulated by particular amino acids. If plasma amino nitrogen levels resulting from infusion of the individual amino acids are very similar, the insulin responses vary considerably. Floyd et al (J Clin Invest 45(9):1487-502), established a decreasing insulin response for the amino acids arginine > lysine > leucine > phenylalanine > valine > methionine. In view of the fact that lysozyme is particularly rich in the amino acid arginine, it is tempting to speculate that an insulin stimulating effect triggered by arginine leads to the high Trp/LNAA ratios. Because carbohydrates are known for their insulin stimulating effect, the hydrolysates according to the present invention are preferably formulated in combination with carbohydrates.

Figure 3:
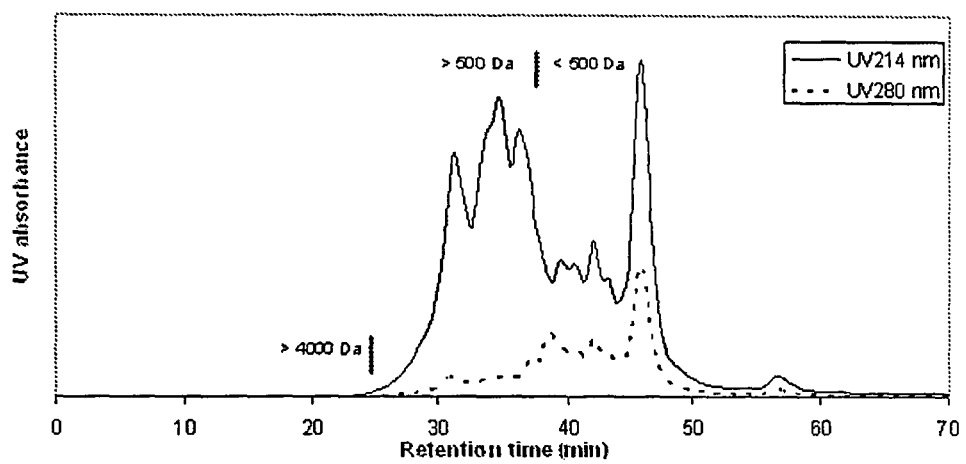

In one embodiment of the present invention, lysozyme, preferably hen egg lysozyme is enzymatically (pre-)hydrolysed in an industrial process i.e. (hen egg) lysozyme is preferably provided in the form of a hydrolysate or an enriched hydrolysate. Offered in the form of such an (enriched) hydrolysate, the intestinal absorbtion of tryptophan containing peptides is greatly facilitated. In another embodiment of the present application, hen egg lysozyme is converted to a hydrolysate or enriched hydrolysate comprising a tryptophan comprising peptide population of which more than 50%, preferably more than 60%, more preferably more than 75% of the peptides present have a molecular weight below 500 Da. Preferably such an (enriched) hydrolysate does not contain more than 1 wt % (on dry matter) of free tryptophan. The molecular weight analysis of the tryptophan comprising peptides present in the hydrolysate is carried out as described in the Materials & Methods section of the present application and is illustrated in FIG. 3. An important advantage of the latter embodiment is that the tryptophan encompassed in di- and tripeptides is transported across the intestinal wall into the blood stream immediately after oral consumption. As a consequence, plasma tryptophan levels are increased almost instantaneously with a direct effect on brain serotonin levels. Quite surprisingly the data presented in Example 6 of the present application show that the efficacy of the tryptophan residues presented in the form of these di- and tripeptides is even more efficacious than free tryptophan. This observation emphasizes the advantages offered by the present invention.

In yet another embodiment of the present application, the (hen egg) lysozyme hydrolysate is fractionated in order to increase the tryptophan content of a fraction of the hydrolysate. This fraction or enriched hydrolysate has preferably an increased Trp/LNAA ratio as compared to the hydrolysate before fractionation. The enrichment of the hydrolysate or enriched hydrolysate with additional free tryptophan, also forms part of the present invention. In a preferred option for preparing such an enriched hydrolysate, use is made of our observation that lysozyme incorporates an unusual high amount of the basic arginine and lysine residues. Surprisingly and as a result of selected enzyme incubation conditions i.e.

choosing an endoprotease having the right cleavage preference (such as subtilisin) in combination with incubation conditions that yield a high amount of di- and tri-peptides incorporating tryptophan but almost no arginine or lysine residues, we can produce the enriched lysozyme hydrolysate according to the invention. Thus, LNAA containing peptides incorporating arginine or lysine residues can be separated from tryptophan containing peptides that do not have such basic residues. For example, by adjusting the pH of the hydrolysate to a value between 4 and 6, more preferably between 5.0 and 5.5, peptides without such a basic residue will have no charge and, therefore, a reduced hydrophilicity. These features can be used to our advantage, for example in a chromatographic or another separation process to selectively remove a large proportion of the arginine or lysine containing peptides. As a result, the content of tryptophan containing peptides is dramatically increased and optionally the Trp/LNAA ratio of this enriched hydrolysate. Charged arginine or lysine incorporating peptides can be removed by known techniques such as ion chromatography, hydrophobic interaction chromatography or electrodialysis. A practical background on the use of such characteristics in the chromatographic separation of the relevant peptides, can be found in a.o. the Protein Purification Handbook (issued by Amersham Pharmacia Biotech, nowadays GE Healthcare Bio-Sciences, Diegem, Belgium). In an even more advanced purification route towards preparations that combine a high tryptophan content with a high Trp/LNAA ratio, the presence of amino acids with acid side groups such as glutamate (Glu) and aspartate (Asp) residues in lysozyme is advantageously used. In this apporach the pH of the lysozyme hydrolysate according to the invention is first adjusted to 3.0 and then chromatographed over a cation resin. At this pH value, peptides incorporating a Glu or Asp will run through the column, other peptides will bind. A subsequent elution with a pH 5 buffer will desorb all bound peptides without a lysine or an arginine residue as described. The majority of the tryptophan containing peptides will be in this desorbed fraction. The remaining bound peptides are then removed from the column by elution with a buffer with an even higher pH value. This elegant approach is illustrated in Example 4 of the present application.

Although for the present invention preferably ion exchange chromatography and/or hydrophobic interaction chromatography are used, other suitable chromatogrographic separation methods comprising affinity chromatography and size exclusion chromatography also are available. The recovery of the tryptophan enriched peptides from resulting aqueous fractions can be done by methods that are known in the art. In order to obtain concentrated and shelf stable products, the recovery preferably incorporates an evaporation and (spray) drying step. Also nanofiltration and extraction processes involving organic solvents followed by evaporation/precipitation steps present options for the desired purification. The recovery of the tryptophan enriched peptides from organic solvents is preferably carried out by evaporation of the solvent.

WO 2006/009448 provides protein hydrolysates obtained from hen egg proteins having antihypertensive properties, as well as food products and food supplements comprising these hydrolysates. This document divulges the preparation of a large number of hydrolysates, including those obtained from hen egg lysozyme. All these hydrolysates aim at reducing blood pressure or preventing blood pressure rises upon oral ingestion in humans. WO 2006/009448 also describes the preparation of lysozyme hydrolysates obtained under alkaline conditions using subtilisin (EC3.4.21.62; commercial names Alcalase or Protex). According to the high degrees of hydrolysis that are obtained, these lysozyme hydrolysates contain a large proportion of peptides with a molecular weight below 500 Da. However, nowhere in the text of WO 2006/009448 reference is made to the fact that lysozyme is a protein source having a high tryptophan content that can positively affect brain serotonin levels. Also not mentioned is that lysozyme hydrolysates comprise water-soluble peptides incorporating a high amount of tryptophan and a relatively low amount of LNAA. WO 2006/009448 also does not mention the high arginine and lysine content of either lysozyme or lysozyme hydrolysates. We have found that on the basis of the data presented in the present application, the high tryptophan content of the lysozyme molecule in combination with the ubiquitous presence of arginine and lysine makes lysozyme the perfect starting material for an in vivo generation of high Trp/LNAA ratios. Furthermore the text of WO 2006/009448 does not mention the advantages offered by the hydrolysate according to the present invention in its co-consumption with other protein containing foods. Apart from the use of membrane filters, the text of WO 2006/009448 also does not mention methods to obtain peptide fractions from these hydrolysates having selected amino acid compositions or using specific methods to increase tryptophan contents or to increase Trp/LNAA ratios. Furthermore the advantage of offering a highly degraded, hypoallergenic lysozyme hydrolysate is not recorded.

Despite the fact that lysozyme turns out to be highly resistant to proteolytic hydrolysis under physiological conditions, i.e. at an acid pH using pepsin, trypsin and chymotrypsin as proteases, lysozyme hydrolysates according to the invention also can be obtained under such less favorable acid conditions. However, under such conditions relatively harsh incubation conditions are required, such as much higher enzyme concentrations, higher temperatures and optionally additional endoproteases.

The data presented in Example 4 of the present application, indicate that the lysozyme hydrolysate obtained by incubating lysozyme at an alkaline pH with subtilisin is particularly rich in the Ala-Trp (AW) dipeptide. This finding suggests that a chemically synthesized AW dipeptide could provide a suitable alternative for the present lysozyme hydrolysate. Although the use of a synthetic dipeptide has obvious legislative drawbacks, important advantages are its cost effectiveness and its ideal Trp/LNAA ratio. Theoretically, twenty different tryptophan containing dipeptides are available, but our investigations have shown that the dipeptides Ala-Trp (AW) and Ser-Trp (SW) represent particularly preferred options to enhance plasma Trp/LNAA ratios via a synthetic dipeptide. Production of the AW and SW dipeptides via chemical synthesis is possible using conventional techniques as for instance described in "Peptides: Chemistry and Biology" by N. Sewald and H. D. Jakubke, Eds. Wiley-VCH Verlag GmbH, 2002, Chapter 4. Particular cost-effective methods of chemical peptide synthesis suitable for large-scale production are based on the use of alkylchloroformates or pivaloyl chloride for the activation of the carboxylic group combined with the use of methyl esters for C-terminal protection and benzyloxycarbonyl (Z) or tert-butyloxycarbonyl groups for N-protection. A detailed procedure for a cost effective synthesis of dipeptide SW is provided in Example 5.

Having lysozyme hydrolysates according to the present invention available, other new and surprising applications are envisaged which have technical and economical advantages.

A new use would be the incorporation of the peptides of the invention in various infant formula products. Cow's milk contains 20% whey protein and human milk 40 to 60%. As a consequence, cow's milk contains less alpha-lactalbumin and thus tryptophan as human milk. Normal, full-term infants are usually fed cow's milk based formulas, products that do not provide an amino acid profile equivalent to that of mother's milk. Although the consequences of an insufficient tryptophan supply are not fully known, infant formula products high in tryptophan, may have benificial effects on conscious behaviour and sleep onset and quality of the infant. A strong indication that a high plasma tryptophane level promotes a quick onset of a quiet sleep in healthy newborns was provided by Yogman and Zeisel in N Engl J. Med. 1983 Nov. 10; 309(19):1147-1149. Accordingly, the present invention provides compositions for infant formula products in which the tryptophan level has been raised using an (enriched) hydrolysate obtained from (hen egg) lysozyme. Preferably, the (hen egg) lysozyme used in such infant formula products is hydrolysed to such an extent that allergenicity issues are prevented, i.e. hen egg lysozyme is preferably provided in the form of a hypoallergenic hydrolysate. According to another aspect of the invention the (enriched) hydrolysates according to the invention can be used in meal replacement products. For example, WO 2005/023017 describes the advantages of gelatin in high dosages as a suitable component in meal replacement products. While providing excellent organoleptic properties, the gelatin does not provide the required amino acid balance, for example, it does not incorporate the essential amino acid tryptophan. So in order to arrive at a composition having the proper balance of amino acids as required by EC Directive 96/8/EC, tryptophan has to be added to such gelatin comprising compositions. In WO 2005/023017 tryptophan is preferably added in the form of tryptophan rich protein, e.g. egg white powder or whole egg powder. We have now found that the tryptophan containing hydrolysates according to the present invention offer an improved solution to this problem as these hydrolysates supply tryptophan in a much more concentrated form. Moreover, lysozym itself contains all essential amino acids at the required amount, and as such is a nutritionally complete protein that ideally fits in a meal replacer.

According to yet another aspect of the invention, the hydrolysates according to the invention are used to stimulate appetite. Quite surprisingly we have found that preparations with a high Trp/LNAA ratio will stimulate plasma ghrelin levels. Ghrelin is known as a "hunger' hormone and stimulating ghrelin production has been shown to increase food intake and body weight in man (Wren et al., 2001, J Clin Endocrinol Metab 86, 5992-5995). Because of this unexpected effect, the hydrolysates according to the invention offer advantages in, for example, clinical food as the critically ill tend to refrain from all food hereby slowing down their recovery.

According to yet another aspect of the invention, the hydrolysates according to the invention are used to improve sleep onset and quality in infants, children and adults. Sleep problems are very prevalent among individuals belonging to various age groups and are associated with medical disorders. The hydrolysates according to the present invention are useful to treat sleep problems in general but they present a useful tool to overcome problems connected with cognitive, psychological, social and behavioural disturbances. Examples are the establishment of a good sleep hygiene, overcoming a sleep-onset association or a circadian rythym sleep disorder. The products also can be useful in improving sleep onset and quality and mental state of, for example, fibromyalgia patients. Fibromyalgia syndrome is a chronic pain syndrome that is related to severely disturbed sleep onset and quality and emotional stress. We have found that a regular intake of the tryptophan enriched hydrolysates according to the invention improves the sleep onset and quality of individuals suffering from sleep problems in general.

The tryptophan containing hydrolysates according to the present invention offer additional advantages such as the supply of (semi-) essential, amino acids. Lysozyme has not only a high tryptophane level but incorporates a significant number of tyrosine residues as well. Tyrosine is the precursor for the neurotransmittor dopamine and it is known that plasma tyrosine levels affect the dopamine levels in the brain. Lysozyme hydrolysate contains not only less LNAA's than other known high-tryptophan peptides, it also contains less branched-chain amino acids (BCAA's) than other known high-tryptophan peptides. This is important since BCAA's are known to lower the plasma availability of the dopamine precursor tyrosine. So, its high Trp/LNAA ratio in combination with its high Tyr/BCAA ratio, makes lysozyme a unique molecule. Therefore, the lysozyme hydrolysate according to the invention is very well placed as a 'brain food", that is, for the supply of the essential amino acids required for proper neurotransmittor levels. The dopamine system is known for its critical role in mediating reward and motivation and its effects on concentration, memory, alertness, attention, problem solving and psychomotor coordination. As illustrated in Example 9 of the present application, the intake of the lysozyme hydrolysate according to the invention has significant beneficial effects on vigilance, alertness, concentration and psychomotor coordination. This finding demonstrates that the lysozyme hydrolysate according to the invention can be expected to stimulate not only the serotonine system, but also the dopamine system.

Several groups of individuals can benefit from this finding. For example, women during their menopausal years have general complaints about their reduced capability for problem solving which they relate to an inability to concentrate. Therefore, the lysozyme hydrolysate according to the invention is especially suited to fight these problems in women of this age group. In the category of young and middle-aged women, the premenstrual syndrome is quite common. The syndrome is characterized by a wide variety of symptoms, but complaints about depression and mood lability are frequently occurring. To fight these phenomenons, selective serotonin reuptake inhibitors such as fluoxetine are frequently prescribed and, in women with milder symptoms, dietary adaptations and prevention of stress. On the basis of the outcome of the experiments described in Examples 6 and 9 of the present application, the lysozyme hydrolysate according to the invention presents an excellent treatment for, especially such milder cases. Furthermore, insufficient dopamine is associated with the attention-deficit hyperactivity disorder (ADHD) so that the symptoms of this disorder can be expected to be aleviated by the lysozyme hydrolysate. Our findings that the beneficial effects on post-stress performance are especially prominent in stress-resistant subjects is surprising. A possible explanation may be that stressed people, with an (over-)active serotonin system, need the tryptophane from the drink to replenish their serotonin stores and thus cannot use this tryptophane for improving their performance in the tasks. According to that line of reasoning, stress-resistant people without an overactive serotonergic system do not need tryptophane to replenish their serotonin stores and can use it to improve their post-stress performance. An alternative explanation may be that these effects are in fact due to a stimulatory effect of dopminergic processes. Dopamine synthesis can be enhanced by food ingredients rich in tyrosine, particularly if combined with low levels of branched-chain amino acids (BCAAs). These working hypotheses are disclosed herein to explain the experimental data shown in the Examples and are used to give the present insight of the inventors. However, the present invention is no way linked or limited to these hypotheses. So the present invention stands independent of the correctness of these hypotheses. As stated elsewhere, lysozyme has not only a high tryptophane level but incorporates a significant number of tyrosine residues as well.

The (enriched) hydrolysates according to the present invention also raise the cysteine content in food products. Although not an essential amino acid, cysteine concentrations are limiting in many food products. The endogeneous synthesis of cysteine requires the presence of methionine and, like cysteine, methionine concentrations are limiting in many food products. The advantages of an increased cysteine content of foods relate amongst others to the an antagonistic effect on the serum homocysteine elevating effect of methionine. This finding has been described in WO 03/055335. The lysozyme hydrolysates according to the invention are also characterized by a high cysteine level. In fact, the lysozyme molecule contains even more cysteine residues (8) than tryptophan residues (6). In this respect the hydrolysates according to the present invention form an excellent source for increasing the cysteine content of certain products. Increased cysteine contents are found to be important for products such as infant formula. Not only infant formula based on casein or mixtures of casein and whey proteins but also for soy based products and in fact for all protein rich products in which the main source of the protein is provided by a protein containing relatively low amounts of tryptophan or cysteine. Apart from the protein components from bovine milk and gelatin, maize protein, yeast protein, pea protein, soy protein and rice protein represent examples of such proteins. Furthermore, the above mentioned meal replacement products containing high dosages of gelatin contain inadequate amounts of cysteine.

The (enriched) protein hydrolysates according to the present invention, or peptide fraction obtained from this protein hydrolysate, or a di- or tripeptide which comprise tryptophan, especially SW or AW, can be used in any suitable form such as a food or a beverage, as Food for Special Nutritional Uses, as a dietary supplement, as a neutraceutical or even in feed or pet food. The lysozyme hydrolysate may be added at any stage during the normal process of these products. If used in food or beverages, products with a relatively low protein content are preferred in order to maintain the high Trp/LNAA ratio in blood after consumption of the products according to the invention. In addition, preferably carbohydrates are added to food or beverages containing lysozyme hydrolysate to even further improve the high Trp/LNAA ratio in blood after consumption. Suitable food products include e.g. cereal bars, bakery items such as cakes and cookies and also liquid foods such as soups or soup powders. Apart from dairy products such as milk and yogurt, other suitable beverages encompass non-alcoholic and alcoholic drinks as well as liquid preparations to be added to drinking water and liquid food. Non-alcoholic drinks are preferably mineral water, sport drinks, fruit juices, lemonades, teas, concentrated drinks such as shots, energy drinks (for example drinks containing glucuronolactone, caffeine or taurine) and carbonated beverages (for example pops, sodas and cola drinks). Preferred combinations of the tryptophan hydrolysate according to the invention are with compounds recommended for "brain nutrition" such as iron, zink, magnesium, vitamins (especially B2, B6, folic acid and C), omega-3 and DHA fats or fatty acids, glucose, GABA, choline, phosphatidyl serine, co-enzyme Q10, creatine, taurine and 5-HTP, or with compounds recommended for relieving stress or depression such as valerian, chocolate, St John's worth, 5-HTP, phosphatidyl serine, alcohol, lemon balm, green tea or green tea extracts, chamomile or S-adenosyl methionine, or with compounds recommended for improving alertness such as caffeine, guarana, ginseng, gingko bilboa, St John's worth, and 5-HTP or with compounds recommended for mood improvement such as GABA, 5-HTP, PEA, green tea or green tea extracts, gingko bilboa, Salvia or S-adenosyl methionine or with compounds recommended for improving sleep such as milk peptides, free tryptophan, opoid peptides or melatonin. Examples of Foods for Special Nutritional Uses include the categories of sport foods, slimming foods, infant formula and clinical foods. The term dietary supplement as used herein denotes a product taken by mouth that contains a compound or mixture of compounds intended to supplement the diet. The compound or mixture of compounds in these products may include: vitamins, minerals, herbs or other botanicals and amino acids. Dietary supplements can also be extracts or concentrates, and may be found in many forms such as tablets, capsules, softgels, gelcaps, liquids, or powders. The term neutraceutical as used herein denotes the usefulness in both the nutritional and pharmaceutical field of application. The neutraceutical compositions according to the present invention may be in any form that is suitable for administrating to the animal body including the human body, especially in any form that is conventional for oral administration, e.g. in solid form such as (additives/supplements for) food or feed, food or feed premix, tablets, pills, granules, dragées, capsules, and effervescent formulations such as powders and tablets, or in liquid form such as solutions, emulsions or suspensions as e.g. beverages, pastes and oily suspensions. Controled (delayed) release formulations incorporating the hydrolysates according to the invention also form part of the invention. Furthermore, a multi-vitamin and mineral supplement may be added to the neutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

In a preferred aspect of the present invention the compositions may be used as a nutritional supplement, e.g. for mood improvement or for the improvement of cognitive functions such as learning, memory, vigilance and alertness for example in elderly people, but also younger people such as students who are preparing exams and for persons playing, for example, computer or internet games. As mentioned before, for pre- and post menopausal women the compositions according to the invention are of particular relevance. The compositions according to the invention are also of particular relevance for sports people; both professional athletes with demanding training schemes, as well as recreational sports people such as people playing tennis or golf. This means that the present invention relates to the use of the hydrolysates according to the invention as given above and as "condition improver", i.e. as means to reduce irritability and tiredness (eventually reducing the risk for overtraining), to reduce or prevent or alleviate physical and mental fatigue, to favour undisturbed sleep, that is to act against insomnia and sleep disorders and to improve sleep, and to increase energy in more general terms, especially to increase the brain energy production, in diseased or normal healthy individuals. Moreover for cognition improvement in general, and especially for maintenance or improvement of attention and concentration, of the memory and of the capacity for remembering, of the learning ability, of the language processing, of problem solving and of intellectual functioning; for improvement of the short-term as well as long-term memory; for increasing the mental alertness; for enhancing the mental vigilance; for reducing the mental fatigue; for supporting cognitive wellness, for maintaining balanced cognitive function. Furthermore, the present invention relates to the use of the hydrolysates according to the invention for increasing appetite. If required for obtaining cost effective preparations with a high Trp/LNAA ratio, the hydrolysates according to the invention optionally comprise free tryptophan.

LEGENDS TO THE FIGURES

FIG. 1 The molar Trp/LNAA ratio in plasma as a function of time after consumption of the products detailed in Example 6. REF=casein hydrolysate, ALAC=intact alpha-lactalbumin, Trp=free tryptohan, WEPS=tryptophan-enriched lysozyme hydrolysate, SYN=synthetic dipeptide Ser-Trp.

Figure 2:
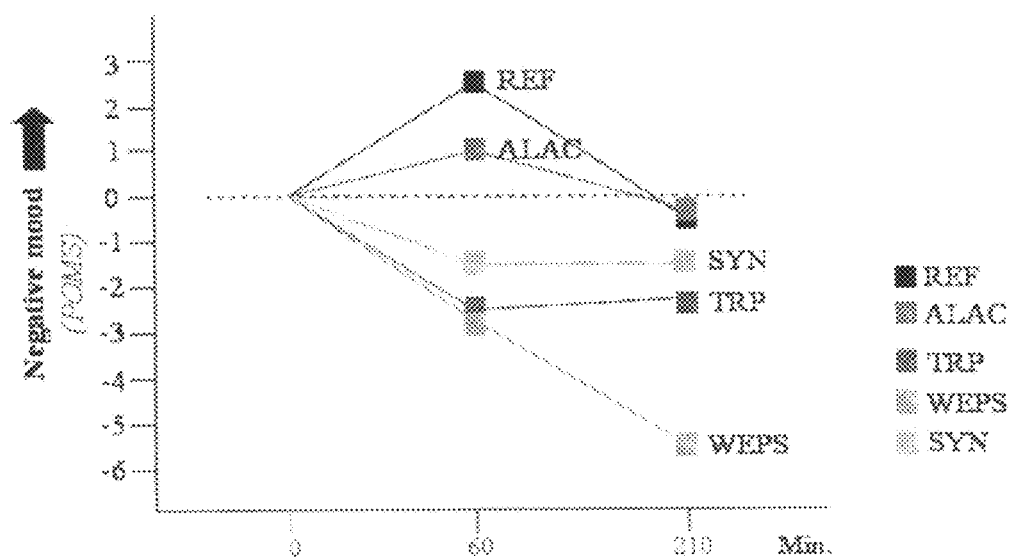

FIG. 2 Negative mood (as measured with the Profile of Mood States test (POMS)) as a function of time after consumption of products detailed in Example 6. REF=casein hydrolysate, ALAC=intact alpha-lactalbumin Trp=free tryptohan, WEPS=tryptophan-enriched lysozyme hydrolysate, SYN=synthetic dipeptide Ser-Trp.

FIG. 3 Size distribution of the water-soluble peptide fraction of a lysozyme hydrolysate. Using the method for determining molecular weight distribution of peptides and proteins present in hydrolysates as detailed in the Materials and Methods section, a lysozyme hydrolysate prepared according to the method described in Example 3 was analyzed. Absorbancy measurements at 214 nm record the presence of peptide bonds. Absorbancy measurements at 280 nm record the presence of the aromatic side chains of tryptophan and tyrosine. As tryptophane has a much higher molar absorptivity than tyrosine at this wavelength, peak values will refer to tryptophan incorporating peptides mainly.

Figure 4:
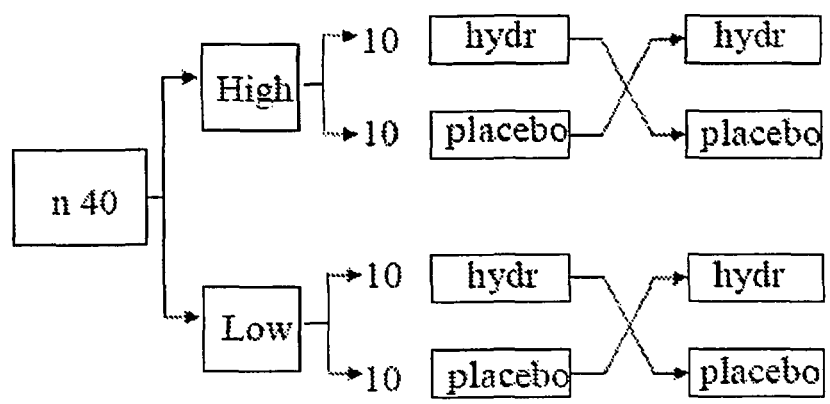
Figure 5:
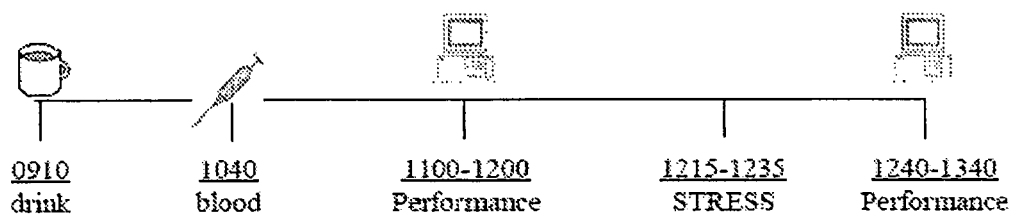

FIG. 4. Flow diagram of the study design of the experiment described in Example 9. High: stress-susceptible volunteers; low: stress-resistant volunteers; hydr::Trp-rich lysozyme hydrolysate; placebo: casein hydrolysate FIG. 5. Flow diagram of a typical study day of the experiment described in Example 9. Drink: consumption of drink containing Trp-rich hydrolysate or placebo; blood: blood sampling for assessment of plasma amino acid levels; performance: performance tests before and after uncontrollable stress; stress: arithmetic task.

Figure 6:
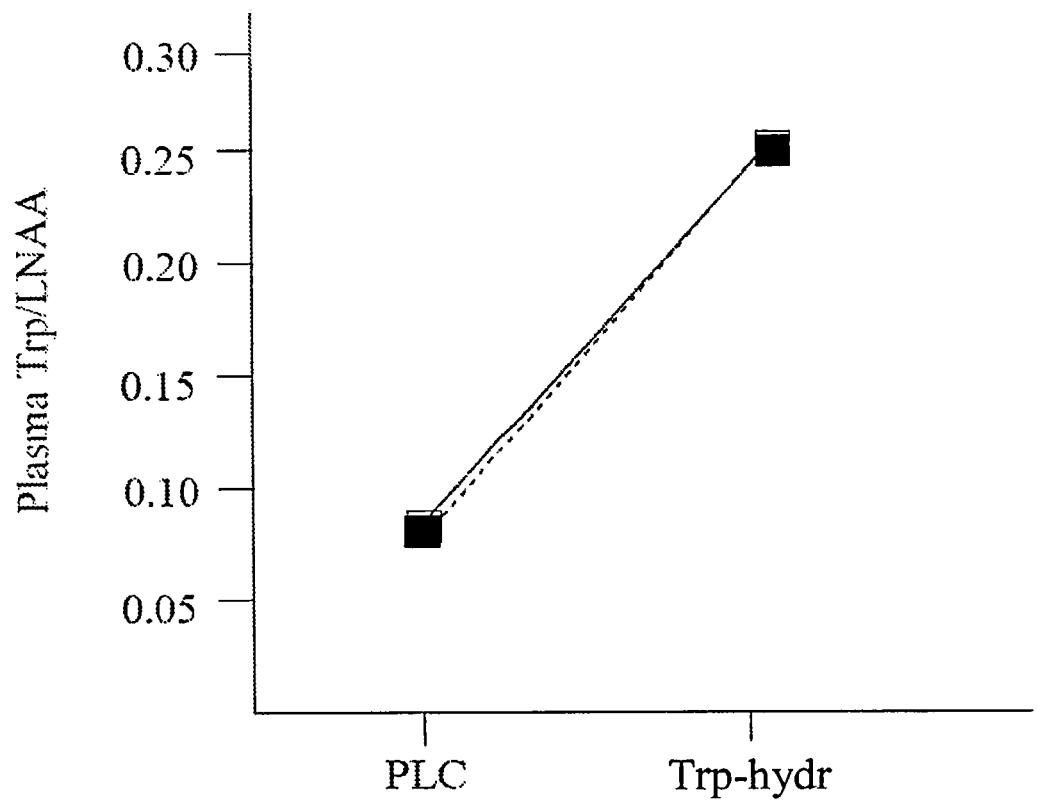

FIG. 6. Plasma Trp/LNAA ratios (μmol/l) following ingestion of placebo (plc) or the lysozyme hydrolysate (Trp-hydr) of the experiment described in Example 9. Black symbols: stress-susceptible subjects; open symbols: stress-resistant subjects.

Figure 7:
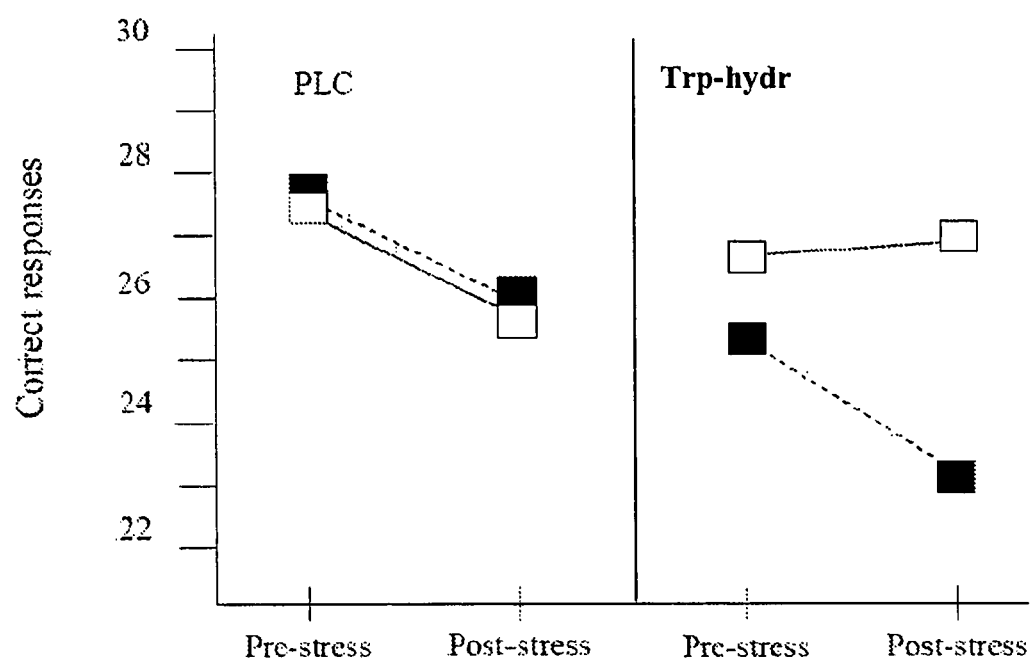

FIG. 7. Results of the Mackworth Clock Test carried out as described in Example 9. The number of correct responses (vertical axis) after consumption of placebo (plc; left-hand panel) or Trp-rich hydrolysate (Trp-hydr; right-hand panel), before (Pre-stress) or after (Post-stress) the arithmetic task. Black symbols: stress-susceptible subjects; open symbols: stress-resistant subjects. Since different intervention products were given on separate days, relevant comparisons may only be made between pre-stress and post-stress conditions within the same treatment and day.

Figure 8:
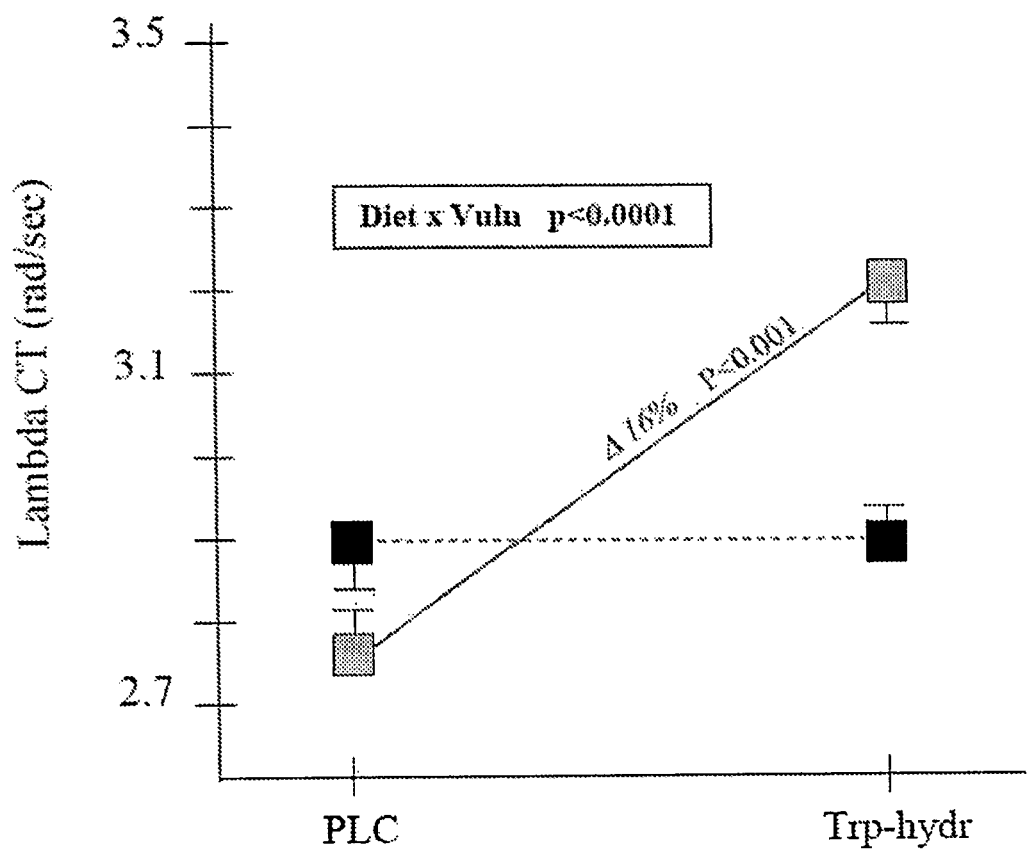

FIG. 8. Results of the Critical Tracking Task carried out as described in Example 9. Lambda CT (indicating the final level of complexity that is reached by the subjects) is expressed after intake of placebo (plc) or Trp-rich hydrolysate (Trp-hydr). Black symbols: stress-susceptible subjects; grey symbols: stress-resistant subjects.

MATERIALS AND METHODS

Materials

Subtilisin under the commercial name of "Protex 6L" was obtained from Genencor (Leiden, The Netherlands), pepsin from Sigma and the mixture of trypsin/chymotrypsin (Porcine PEM) from Novozymes (Bagsvaerd, Denmark). Lysozyme was obtained as Delvozyme L (22% dry matter) from DSM Food Specialities (Delft, The Netherlands). Casein hydrolysate ("REF") was obtained essentially as described by Edens et al (J Agric Food Chem, 53(20)7950-7957, 2005). Sodium caseinate was extensively hydrolysed with Protex 6L and, after lowering the pH to 4.5, with a proline specific endoprotease to reach a DH>20%. Following ultrafiltration, the permeate was heat treated to inactivate any remaining enzymatic activities and finally spray dried. Intact alpha-lactalbumin ("ALAC") was obtained as "Biopure" (>90% alpha-lactalbumin) from Davisco Foods International, Inc. (Le Seuer, Minn.); tryptophan-enriched lysozyme hydrolysate ("WEPS") was obtained as described in Example 4; the synthetic Ser-Trp dipeptide ("SYN") was obtained as described in Example 5; pure L-tryptophan ("TRP") was obtained as L-tryptophan-400 from Orthica, Almere, The Netherlands.

SDS-PAGE

The purity of the lysozyme preparations used was checked by SDS-PAGE. All materials used for SDS-PAGE and staining were purchased from Invitrogen (Carlsbad, Calif., US). Samples were prepared using SDS buffer according to manufacturers instructions and separated on 12% Bis-Tris gels using MES-SDS buffer system according to manufacturers instructions. Staining was performed using Simply Blue Safe Stain (Collodial Coomassie G250). Prior to hydrolysis the lysozyme appeared as a single band with a molecular weight of approx. 14 kDa on the gel.

LC/MS/MS Analysis

HPLC using an ion trap mass spectrometer (Thermo Electron, Breda, the Netherlands) coupled to a P4000 pump (Thermo Electron, Breda, the Netherlands) was used to determine the presence of tryptophan containing peptides (mainly di- and tri peptides) in the enzymatic protein hydrolysates produced by the process according to the invention. The peptides formed were separated using an Inertsil 3 ODS 3, 3 μm, 150*2.1 mm column (Varian Belgium, Belgium) in combination with a gradient of 0.1% formic acid in Milli Q water (Millipore, Bedford, Mass., USA; Solution A) and 0.1% formic acid in acetonitrile (Solution B) for elution. The gradient started at 100% of Solution A, kept here for 10 minutes, increasing linear to 20% B in 25 minutes and immediately going to the starting conditions, and kept here 15 minutes for stabilization. The injection volume used was 50 microliters, the flow rate was 200 microliter per minute and the column temperature was maintained at 55° C. The protein concentration of the injected sample was approx. 50 micrograms/milliliter. Identification of the peptides of interest is based on the retention time, protonated molecule and by using dedicated MS/MS for the peptides of interest, using optimal collision energy of about 30%. Quantification of specific tryptophan containing peptides is performed by using an external standard method. The tetra peptide VVPP (M=410.2) was used to tune for optimal sensitivity in MS mode and for optimal fragmentation in MS/MS mode, performing constant infusion of 5 μg/ml, resulting in a protonated molecule in MS mode, and an optimal collision energy of about 30% in MS/MS mode, generating a B- and Y-ion series.

Prior to LC/MS/MS the enzymatic protein hydrolysates were centrifuged at ambient temperature and 13000 rpm for 10 minutes and the supernatant was diluted 1:100 with demineralised water filtered through Millipore water filtration equipment (MilliQ water).

Amino Acid Analyses

The amino acid profiles in plasma were analyzed as described in Example 6 by HPLC according to van Eijk et al (J. Chromatogr. 1993:620:143-148).

Other amino acid analyses were carried out according to the PicoTag method as specified in the operators manual of the Amino Acid Analysis System of Waters (Milford Mass., USA). To that end samples were dried and directly derivatised using phenylisothiocyanate. The derivatised amino acids present were quantitated using HPLC methods as described. As during the usual acid hydrolysis Trp and Cys are destroyed, special methods were used to quantitate these two amino acids. To prevent Cys degradation during hydrolysis, this amino acid is first oxidized to cysteic acid using hydrogen peroxide and then quantitated. The analysis of tryptophan is based on a slightly modified Waters procedure. In this procedure an aliquot of the peptide solution is dried under vacuum and then hydrolysed during 1 hour at 150 degrees C. under nitrogen in 4M methane sulphonic acid containing 0.2% tryptamine. The reaction product is directly quantitated using HPLC equipped with an Alltech Altima C18 column and fluorescence detection.

Degree of Hydrolysis

The Degree of Hydrolysis (DH) as obtained during incubation with the various protolytic mixtures was monitored using a rapid OPA test (Nielsen, P. M.; Petersen, D.; Dambmann, C. Improved method for determining food protein degree of hydrolysis. *Journal of Food Science* 2001, 66, 642-646).

Kjeldahl Nitrogen

Total Kjeldahl Nitrogen was measured by Flow Injection Analysis. Using a Tecator FIASTAR 5000 Flow Injection System equipped with a TKN Method Cassette 5000-040, a Pentium 4 computer with SOFIA software and a Tecator 5027 Autosampler the ammonia released from protein containing solutions was quantitated at 590 nm. A sample amount corresponding with the dynamic range of the method (0.5-20 mg N/l) was placed in the digestion tube together with 95-97% sulphuric acid and a Kjeltab subjected to a digestion program of 30 minutes at 200 degrees C. followed by 90 minutes at 360 degrees C. After injection in the FIASTAR 5000 system the nitrogen peak is measured from which the amount of protein measured can be inferred.

Molecular weight distribution of peptides and proteins present in hydrolysates. Analysis of the peptide size distribution of protease treated protein samples was done on an automated HPLC system equipped with a high pressure pump, an injection device able to inject 10-100 microliter sample and a UV detector able to monitor the column effluent at 214 nm.

The column used for this analysis was a Superdex Peptide HR 10/300 GL (Amersham) equilibrated with 20 mM Sodium Phosphate/250 mM Sodium Chloride pH 7.0 buffer. After injecting a sample (typically 50 microliter) the various components were eluted from the column with buffer in 90 min at a flow rate of 0.5 ml/min. The system was calibrated using a mixture of cytochrome C (Mw 13 500 Da), aprotinin (Mw 6510 Da) and tetra-glycine (Mw 246 Da) as molecular weight markers.

The following Examples illustrate the invention further.

EXAMPLES

Example 1

Hen Egg Lysozyme is not Cleaved by Either Pepsin or Trypsin/Chymotrypsin

To test its digestibility in the human gastrointestinal tract, hen egg lysozyme was incubated in vitro with pepsin as well as with a mixture of trypsin and chymotrypsin. Both incubations were carried out under pH conditions that are prevalent in the stomach (pepsin) and duodenum (trypsin/chymotrypsin). To that end, a 5% (w/w) lysozyme solution was incubated with the enzymes (1% w/w enzyme to lysozyme protein) for 2 hours at 37 degrees C. To prevent major pH changes as the result of the ongoing protein hydrolysis, incubation was carried out in a Mc Ilvane buffer (0.2 M citric acid plus Na2HPO4). The low DH's values that are obtained after the two hours hydrolysis at 37 degrees C. (see Table 1), demonstrate that the lysozyme molecule cannot be degraded under conditions that mimic digestion conditions in the stomach and in the duodenum and jejunum because successful proteolysis can be expected to lead to a DH value of at least 10%. Therefore, tryptophan residues present in the intact hen egg lysozyme molecule will not be liberated in the gastrointestinal tract hereby implying that tryptophan molecules present in intact hen egg lysozyme cannot contribute to plasma tryptophan levels.

TABLE 1

| Lysozyme hydrolysis by pepsin and a trypsin/chymotrypsin mixture | | | | |
|---|---|---|---|---|
| Enzyme | pH start | pH end | DH start (%) | DH end (%) |
| Pepsin | 2.8 | 2.4 | =0 | 2.4 |
| Pepsin | 3.6 | 3.2 | | <1 |
| Pepsin | 4.6 | 4.3 | | 1.0 |
| Trypsin/chymotrypsin | 4.6 | 4.3 | | <1 |
| Trypsin/chymotrypsin | 5.9 | 5.5 | | <1 |
| Trypsin/chymotrypsin | 7.2 | 7.0 | | 1.3 |

Example 2

Hen Egg Lysozyme is Efficiently Cleaved by Subtilisin at Elevated pH Values

To test the susceptibility of lysozyme to enzyme hydrolysis under non-physiological pH and enzyme conditions, a lysozyme solution was incubated in vitro with a microbial subtilisin (EC 3.4.21.62) under alkaline pH conditions. To that end, a 5% (w/w) lysozyme solution was incubated at pH 7.0, 8.0 and 9.0 with 12.5 microliter of Protex 6L.per gram lysozyme protein present. The incubation was carried out for 3 hours at 60 degrees C. with a constant adjustment of the pH using 1M NaOH. The incubations yielded slightly turbid solutions without any significant precipitates. After a heating step to inactivate the subtilisin activity, the DH values of the various incubations were measured according to the protocol described in the Materials & Methods section. In contrast with the results obtained under physiological conditions (see Example 1), alkaline incubation conditions using subtilisin result in complete lysozyme hydrolysis. The pH 7.0 incubation yielded a DH of 6.3, the pH 8.0 incubation a DH of 11.2 and the pH 9.0 incubation a DH of 16.4. A subsequent SDS-PAGE analysis of the reaction products, indicated that the whole lysozyme molecule was degraded i.e. no large molecular weight fragments survived the subtilisin incubation. Furthermore, HPLC analysis of the hydrolysate on a Crownpak CR+ column (Daicel) revealed that no significant racemisation of tryptophan containing peptides took place, not even after prolonged heating at pH 9.0.

Example 3

Hydrolysing Lysozyme Using Protex and Identity of the Peptides Formed

A solution containing 10% (w/w) pure lysozyme was adjusted to pH 8.2 using NaOH and heated to 52 degrees C. Hydrolysis was started by adding 25 microliter of Protex/g of protein present. Under continuous stirring and maintaining the pH at 8.2, the hydrolysis was continued for 5.5 hours to yield an almost clear solution without a visible precipitate. After a heating step to inactivate the Protex activity, a sample was taken for DH analysis. The DH of the solution turned out to be almost 30%. The heat treated solution was ultrafiltered over a 10 kDa filter to yield a completely clear liquid. This clear liquid was used for LC/MS analysis, for molecular weight distribution of peptides and proteins present as well as for ion exchange chromatography.

To get an impression of the molecular weight distribution of peptides and proteins present, the clear liquid was subjected to a molecular size analysis as described in the Materials & Methods section. The results obtained (see FIG. 3), clearly indicate that almost all peptides incorporating amino acids with an aromatic side chain (i.e. tryptophan, tyrosine and phenylalanine) have a molecular weight below 500 kDa. In view of the high molecular weight of these amino acids, the implication is most of these small peptides are either tri- or dipeptides.

LC/MS analysis was carried out according to the procedure as described in the Materials & Methods section. By selecting for those peptides containing a tryptophan ("W"), peptides AW, GNW, WIR, NAW, WVA, VAW, AWR, SLGNW (SEQ ID NO:1) and minor quantities of WW and SRWW (SEQ ID NO:2) could be detected. The level of free tryptophan in the hydrolysate after incubation was established to represent less than 1% of the total (lysozyme) tryptophan present.

As di- and tripeptides are readily absorbed by peptide transporters present in the intestinal wall, there is little doubt that tryptophan residues present in such peptides will be rapidly absorbed and lead to increased plasma tryptophan levels upon oral intake of the present lysozyme hydrolysate.

Example 4

Increasing the Tryptophan Content of the Hydrolysate

Lysozyme incorporates a surprising high amount of the basic arginine and lysine residues. Furthermore the lysozyme molecule incorporates a significant number of the acid glutamate and aspartate residues. This data has been used to devise an innovative and elegant purification route towards hydrolysates featuring high Trp/LNAA ratios. Essential requirement for this purification route is, however, that only very few of the tryptophan residues show up in peptides also containing either an arginine or lysine residue or a glutamate or aspartate residue. As shown in Example 3, the specific hydrolysis route used here yields only few trytophan containing peptides containing an arginine residue and no peptides containing a lysine, glutamate or aspartate residue. Theory predicts that a maximal charge difference between peptides with and without a glutamate or aspartate residue can be achieved around pH 3. A maximal charge difference between peptides with and without an arginine or lysine residue, can be achieved around pH 5.

To illustrate the selective power of this approach, a lysozyme hydrolysate was prepared according to the procedure specified in Example 3. Then, the pH of the hydrolysate was adjusted to pH 3.1 using acetic acid and approximately 0.5 gram of protein was applied to a 15 ml bed volume of SP Sepharose FF (GE Healthcare, Diegem, Belgium) column equilibrated with 20 mm sodium citrate pH 3.1. After washing the column with one column volume of the sodium citrate buffer to remove the majority of the peptides incorporating a glutamate or aspartate, the elution buffer was changed to a 20 mm sodium citrate buffer pH 5.1. During washing of the column with three column volumes of the latter buffer, a range of tryptophan containing peptides was eluted. According to LC/MS analysis, the dipeptide AW was present in large amounts as well as the tripeptides GNW, NAW, WVA, VAW and a small amount of the pentapeptide SLGNW. Amino acid analysis of the various pH 5.1 fractions showed that selective pooling yielded a solution having a molecular Trp/LNAA ratio of 1.75 and a tryptophan yield of almost 30%. A less selective pooling yielded a solution with a molecular Trp/LNAA ratio of 0.4 and a tryptophan yield of 70%. Subsequently, the column was washed with three column volumes 20 mM sodium citrate pH 7.1. According to the LC/MS data, this step eluted arginine containing peptides WIR, AWIR and, surprisingly, peptide WW. A final washing of the column with 1 M of NaOH, water and 1M of acetic acid prepared the column for a next run.

Example 5

Chemical Synthesis of Dipeptide Ser-Trp

The dipeptide Ser-Trp was synthesized according to standard peptide technology. In a first step Z-Ser-OH and Trp-OMe were coupled via the carbonic anhydride methodology (J. Am. Chem. Soc. 1967, 5012) to yield the protected dipeptide Z-Ser-Trp-OMe. To that end Trp-OMe.HCl was suspended in tetrahydrofuran (THF) and subsequently N-methylmorpholine (NMM) was added. The mixture was stirred for one hour and subsequently added to a solution of Z-Ser in tetrahydrofuran/dimethylformamide (THF/DMF). A second equivalent of NMM was added and the mixture was cooled to −15° C. Isobutyl chloroformate is added at such a rate that the internal temperature does not exceed −15° C. Subsequently, the mixture was stirred for 3 hours, the temperature was allowed to rise to ambient temperature and the precipitated NMM.HCl was removed by filtration. The filtrate was kept at 4° C. overnight after which any additional precipitate was filtered and the filtrate is concentrated in vacuo. The residue was purified by column chromatography ($SiO_2$, ethyl acetate/heptane). The combined fractions were concentrated, washed with water to remove any remaining DMF and concentrated in vacuo.

In a second step, enzymatic hydrolysis of Z-Ser-Trp-OMe was accomplished using Alcalase 2.5L DX (Int. J. Peptide Protein Res. 1990, 52) and subsequent catalytic hydrogenolysis provided the desired peptide as an off-white solid. To that end the purified Z-Ser-Trp-OMe was dissolved in tBuOH and water and Alcalase 2.5 L DX (Novozymes, Bagsvaerd, Denmark) was added. The mixture was stirred until (almost) all starting material was consumed. The mixture was then concentrated in vacuo and the residue taken up in water of pH 7. The aqueous mixture was extracted with ethyl acetate to remove any remaining starting material and subsequently the aqueous phase was acidified. The desired product, i.e. Z-Ser-Trp-OH, was isolated by extraction with ethyl acetate; the extract was dried over sodium sulphate and concentrated in vacuo.

In a third step, dipeptide Ser-Trp-OH was obtained. To that end the concentrated Z-Ser-Trp-OH was dissolved in MeOH and water (1:1), Pd/C was added and the mixture was stirred under a postive hydrogen atmosphere (5 bar). Upon completion of the reaction, the catalyst plus the majority of the product was removed by filtration and the filtrate discarded. The filter was washed extensively with milliQ water and the filtrate concentrated in vacuo, yielding the dipeptide Ser-Trp-OH as a white to off-white solid. Additional purification was achieved by stirring the product in a mixture of acetone-water and isolation of the peptide by filtration. This yielded a product suitable for oral consumption.

Example 6

Effects of Different Tryptophan Sources on Plasma Trp/LNAA Ratios and Mood in Healthy Volunteers The aim of the present study was to investigate in healthy volunteers plasma Trp/LNAA profiles and mood after the consumption of different tryptophan containing preparations. The following preparations were tested:
  intact alpha-lactalbumin (see Materials & Methods)
  hydrolyzed caseinate (DH>20%; see Materials & Methods)
  a Trp-enriched lysozyme hydrolysate with a high Trp/LNAA ratio (see Example 4)
  a synthetic SW dipeptide (Example 5)
  free L-tryptophan (see Materials & Methods).

Eighteen healthy students (9 males and 9 females: age between 18-30 years) participated in the study. Exclusion criteria for participation were chronic and current illness, history of psychiatric or medical illness, use of medication or drugs, alcohol consumption (>2 units/day), metabolic-, hormonal- or intestinal diseases and irregular diets or deviant eating habits (assessed by health and life-style questionnaires). Subjects participating in the experiment were in the normal range for the Body-Mass Index (BMI in kg/m$^2$ between 20-25) and female subjects are matched for contraception. Women participated during their mid-late follicular phase (day 4-10), while women using contraception participated when they actually used the contraception pill. Participants were non-smokers and did not use any alcohol before and during the study. All subjects participating in the experiment signed an Informed Consent Form. This study was conducted according to the EC principles of Good Clinical Practice (GCP) adopted by the 52$^{nd}$ WMA General Assembly, Edinburgh, Scotland, October 2000.

Subjects were instructed to fast overnight; only water or tea without sugar was permitted. During five experimental morning sessions, subjects visited the laboratory to monitor plasma Trp/LNAA concentrations and mood following the intake of a drink containing different Trp or LNAA concentrations. The order of presentation of the various drinks was counterbalanced and the four experimental days were separated by a one-week period. On each experimental morning, a 312 ml drink was provided containing different tryptophan (Trp) or LNAA concentrations (Table 1). All drinks contained 0.10 g sweetener (acesulfame) and were filled up with plain water in order to reach 312 mL. A research assistant blind to the dietary conditions conducted the administration of the different drinks.

TABLE 1

Protein/amino acid composition of drinks used

| Protein source | Casein Hydrol. | Intact Alpha-lac | Trp-enhanced lysozyme hydrol. | Ser-Trp | Free L-Trp |
|---|---|---|---|---|---|
| Code used | REF | ALAC | WEPS | SYN | TRP |
| grams | 20 | 20 | 300 ml solution | 1.20 | 0.82 |
| Trp (g) | 0.40 | 0.80 | 0.80 | 0.80 | 0.80 |
| Trp/LNAA (molar) | 0.04 | 0.10 | 1.1 | ∞ | ∞ |

Blood samples were collected in duplicate before and 15, 30, 60, 90, 120, 180 and 210 minutes after ingestion in 5 ml vacutainer tubes containing sodium heparine and were then centrifuged at 5000 rpm for 5 min at 4° C. The resulting supernatants were mixed with sulfasalicyl acid (4 mg/100 microliter) and directly stored at −80° C. until analysis. Plasma amino acid analysis was conducted with HPLC, making use of a 2-3 µm Bischof Spherisorb ODS II column as described by van Eijk et al (J. Chromatogr. 1993:620:143-148). The plasma Trp/LNAA ratios were calculated by dividing the plasma molar tryptophan concentration by the sum of the plasma molar concentrations of the large neutral amino acids valine, isoleucine, leucine, tyrosine and phenylalanine. Statistical analysis took place by means of repeated measures multivariate and univariate analyses of variance (MANOVA and ANOVA) using the General Linear Model (GLM: SPSS 12.0 for Windows). All statistics were evaluated at a significance level of P=0.05.

Plasma Trp/LNAA Values

A first repeated measures analysis of variance with Condition and Time as within-subjects factors on the plasma Trp/LNAA ratio revealed a main significant effect of Time and Condition and a significant interaction Condition×Time. The highest significant increases in plasma Trp/LNAA ratio were found (see FIG. 1) after providing "SYN" (increase 263% after 60 min) and "WEPS" (increase 255% after after 90 min). The increase in Trp/LNAA after these two products, was significantly faster and higher than after intake of either "TRP" (increase 191% after 120 min) or "ALAC" (increase 67% after 120 min). After consumption of "REF", there was a significant decline in Trp/LNAA starting 60 min until 210 min (−27%).

The 255% rise in Trp/LNAA as found with "WEPS" considerably exceeds the 50-70% increases as previously found with intact alpha-lactalbumin (Markus et al., 2000; Booij et al., 2006) and all earlier reported 20-45% increases with other foods like carbohydrates (Markus, 2003). While a 40-50% variation in plasma Trp/LNAA is thought to be sufficient to change Trp levels and 5-HT synthesis and release in the brain (Markus et al., 2000), this 255% rise is expected to cause a much larger rise in available brain Trp and 5-HT and therefore may also result in a greater release of functionally active brain 5-HT.

Profile of Mood States (POMS).

Mood changes of the various participants were measured using a paper-and-pencil version of the Dutch shortened version of the Profile of Mood States questionnaire (Wald and Mellenbergh, Ned Tijdschr Psychol 1990:45:86-90) as a VAS scale ranging from 'strongly disagree' to 'strongly agree'. The POMS comprises five different subscales for mood; ranging from Anger, Depression, Fatigue and Tension that refer to a negative mood state, to Vigor concerning a positive mood.

Repeated measures analysis of variance with Condition and Time as within-subjects factors on the total mood scores revealed a significant effect of Time and a significant interaction of Condition×Time; indicating that mood changes across time significantly differed between conditions. Comparable improvements of mood were found 60 min after the intake of "WEPS" and "TRP", but only with "WEPS" mood further improved until 210 min after intake as compared with "TRP". In contrast, no mood changes were found after the intake of "REF" and "ALAC". The absence of a mood effect after intact alpha-lactalbumin is comparable with previous studies showing mild beneficial effects on mood after intact alpha-lactalbumin and only in stress-vulnerable subjects under acute stress exposure (Markus et al., 2000; Markus et al., 2000, Markus, 2003). Although mood also seemed to improve after intake "SYN", this effect was not significant in this experimental set up.

These current results suggest that a large 255% increase in plasma Trp/LNAA may be sufficient for an improved mood in normal non-stress-vulnerable subjects. Based on previous findings it is expected that these beneficial effects of the Trp-enhanced lysozyme hydrolysate on mood will be even greater in stress-vulnerable subjects under high mental stress conditions (Markus, 2003). Contrary to our expectations, there were no significant improvements in mood after intake of the synthetic dipeptide. This unexpected result may be attributable to the current experimental set up or to differences in tryptophan bioavailability from these various sources.

TABLE 2

Changes in plasma amino acid concentrations (μmol/l) in time after ingestion of casein hydrolysate ("REF"), intact alpha-lactalbumin ("ALAC") or Trp-enhanced lysozyme hydrolysate ("WEPS").

| Amino acid | Condition | 0 | 30 | 60 | 90 | 120 | 180 | 210 |
|---|---|---|---|---|---|---|---|---|
| Isoleucine | REF | 0.07 | 0.10 | 0.18 | 0.15 | 0.12 | 0.09 | 0.08 |
| | ALAC | 0.08 | 0.12 | 0.20 | 0.22 | 0.18 | 0.12 | 0.11 |
| | WEPS | 0.07 | 0.09 | 0.09 | 0.14 | 0.09 | 0.08 | 0.09 |
| Leucine | REF | 0.12 | 0.19 | 0.31 | 0.26 | 0.22 | 0.17 | 0.16 |
| | ALAC | 0.13 | 0.22 | 0.37 | 0.38 | 0.28 | 0.21 | 0.20 |
| | WEPS | 0.13 | 0.14 | 0.14 | 0.13 | 0.13 | 0.13 | 0.14 |
| Phenylalanine | REF | 0.06 | 0.08 | 0.10 | 0.08 | 0.08 | 0.06 | 0.06 |
| | ALAC | 0.07 | 0.09 | 0.11 | 0.10 | 0.09 | 0.07 | 0.07 |
| | WEPS | 0.07 | 0.07 | 0.07 | 0.06 | 0.10 | 0.06 | 0.07 |
| Tyrosine | REF | 0.06 | 0.07 | 0.12 | 0.11 | 0.09 | 0.07 | 0.07 |
| | ALAC | 0.06 | 0.08 | 0.12 | 0.12 | 0.10 | 0.08 | 0.08 |
| | WEPS | 0.06 | 0.07 | 0.07 | 0.06 | 0.06 | 0.06 | 0.06 |
| Valine | REF | 0.24 | 0.28 | 0.45 | 0.42 | 0.38 | 0.32 | 0.30 |
| | ALAC | 0.26 | 0.30 | 0.38 | 0.42 | 0.35 | 0.29 | 0.28 |
| | WEPS | 0.26 | 0.27 | 0.25 | 0.25 | 0.25 | 0.25 | 0.26 |
| Tryptophan | REF | 0.06 | 0.07 | 0.08 | 0.08 | 0.07 | 0.06 | 0.05 |
| | ALAC | 0.07 | 0.09 | 0.18 | 0.23 | 0.19 | 0.13 | 0.12 |
| | WEPS | 0.07 | 0.13 | 0.21 | 0.23 | 0.20 | 0.14 | 0.13 |
| LNAA | REF | 0.52 | 0.67 | 1.14 | 1.01 | 0.86 | 0.73 | 0.65 |
| | ALAC | 0.60 | 0.82 | 1.14 | 1.22 | 1.10 | 0.86 | 0.82 |
| | WEPS | 0.62 | 0.60 | 0.65 | 0.60 | 0.68 | 0.55 | 0.64 |
| Trp/LNAA | REF | 0.11 | 0.09 | 0.08 | 0.08 | 0.08 | 0.08 | 0.08 |
| | ALAC | 0.12 | 0.12 | 0.15 | 0.18 | 0.2 | 0.18 | 0.17 |
| | WEPS | 0.11 | 0.19 | 0.36 | 0.39 | 0.35 | 0.25 | 0.22 |

TABLE 3

Changes in plasma amino acid concentrations (μmol/l) in time after ingestion of free L-Trp ("TRP") or the synthetic dipeptide SW ("SYN").

| Amino acid | Condition | 0 | 30 | 60 | 90 | 120 | 180 | 210 |
|---|---|---|---|---|---|---|---|---|
| Isoleucine | TRP | 0.07 | 0.07 | 0.07 | 0.06 | 0.07 | 0.07 | 0.07 |
| | SYN | 0.06 | 0.07 | 0.06 | 0.06 | 0.06 | 0.06 | 0.07 |
| Leucine | TRP | 0.13 | 0.13 | 0.12 | 0.12 | 0.12 | 0.12 | 0.13 |
| | SYN | 0.11 | 0.14 | 0.12 | 0.12 | 0.12 | 0.12 | 0.13 |
| Phenylalanine | TRP | 0.07 | 0.07 | 0.06 | 0.06 | 0.06 | 0.06 | 0.06 |
| | SYN | 0.06 | 0.07 | 0.06 | 0.06 | 0.06 | 0.06 | 0.06 |
| Tyrosine | TRP | 0.06 | 0.06 | 0.06 | 0.05 | 0.06 | 0.05 | 0.05 |
| | SYN | 0.05 | 0.06 | 0.05 | 0.05 | 0.05 | 0.05 | 0.05 |
| Valine | TRP | 0.25 | 0.25 | 0.23 | 0.22 | 0.23 | 0.22 | 0.23 |
| | SYN | 0.21 | 0.26 | 0.22 | 0.22 | 0.22 | 0.21 | 0.23 |
| Tryptophan | TRP | 0.07 | 0.07 | 0.17 | 0.18 | 0.18 | 0.13 | 0.11 |
| | SYN | 0.06 | 0.13 | 0.21 | 0.18 | 0.15 | 0.11 | 0.10 |
| LNAA | TRP | 0.62 | 0.59 | 0.55 | 0.50 | 0.58 | 0.52 | 0.53 |
| | SYN | 0.50 | 0.58 | 0.48 | 0.47 | 0.45 | 0.48 | 0.54 |
| Trp/LNAA | TRP | 0.11 | 0.12 | 0.29 | 0.31 | 0.32 | 0.24 | 0.20 |
| | SYN | 0.11 | 0.22 | 0.40 | 0.37 | 0.31 | 0.22 | 0.19 |

Example 7

Large Scale Lysozyme Hydrolysis

In larger scale lysozyme hydrolysis procedures, essentially the procedure as described in Example 3 was followed with some minor modifications. A solution containing 7.3% (w/w) pure lysozyme was heated to 65 degrees C. after which the pH was adjusted to pH 8.2 using NaOH. Hydrolysis was started by adding 25 microliter of Protex 6L/g dry matter. Under continuous stirring and maintaining the pH at 8.2 and the temperature at 53 degrees C., the hydrolysis was continued for 2 hours. Then the pH value was increased to 9.0 and incubation was pursued for another 3.5 hours to yield a solution with some precipitate. Then the pH of the solution was lowered to 4.5 and the solution was cooled to below 4 degrees C. To obtain a completely clear product, the liquid was filtered over a Z 2000 filter (Pall) and subsequently excess water and salt was removed via nanofiltration. The resulting concentrate was then subjected to an UHT treatment of 7 seconds at 120 degrees C., evaporated and finally spray dried to obtain the lysozyme hydrolysate in a dry form. The product thus obtained has a molar Trp/LNAA ratio of about 0.19.

Example 8

Preparing a Beverage Incorporating the Lysozyme Hydrolysate

The following recipe illustrates the preparation of an fat-free, lysozyme hydrolysate containing strawberry drink. To 10 grams of lysozyme hydrolysate powder (prepared according to Example 7), 40 grams of glucose, 2.4 grams of citric acid, 0.38 grams of malic acid, 0.15 grams of sucralose and 0.5 grams of strawberry flavor (Buteressence, Zaandam, The Netherlands) were added. This mixture of powders readily dissolves in 1 liter of water to obtain a ready-to-drink beverage with a high Trp/LNAA and a high Tyr/BCAA ratio. The powder mixture is suitable for e.g. sachet filling. Packaged liquid products can be produced using various known technologies.

Example 9

Effects of Lysozyme Hydrolysate on Post-Stress Performance in Stress-Susceptible and Stress-Resistant Healthy Volunteers The aim of the present study was to compare the effects of a lysozyme hydrolysate prepared according to the procedure described in Example 7, with a placebo (casein protein hydrolysate; see Example 6) in terms of plasma Trp/LNAA levels and its consequences on post-stress performance tasks. The performance tests used are known to adress "vigilance" and "eye-motor control" aspects of indivuduals.

Forty individuals, of which twenty males and twenty females, participated in the present study. Based on a pre-study questionnaire, one half of this group was classified as stress-resistant, the other half as stress-susceptible. The in- and exclusion criteria for the individuals as well as the general study conduct, were the same as described in Example 6. A flow diagram of the design of the study is given in FIG. 4 and a schematic of a typical study day is given in FIG. 5.

On the experimental mornings, subjects arrived fasted at the laboratory. Upon arrival, they were given either a drink containing the lysozyme hydrolysate, or the placebo i.e. the drink containing the casein hydrolysate. The composition of test drink and placebo drink is outlined in Table 4.

TABLE 4

Composition of drinks used.

| Protein source | Casein hydrolysate | Lysozyme hydrolysate |
|---|---|---|
| abbreviation | plc | Trp-hydr |
| g powder/300 ml | 13.6 | 14.4 |
| Water | 286 g | 285 g |
| Sweetener | 0.1 g | 0.1 g |
| g Trp/300 ml | 0.4 | 0.8 |
| Trp/LNAA ratio (molar) | 0.04 | 0.19 |

Ninety minutes after consumption of the 300 ml drinks, a blood sample was taken to assess Trp/LNAA ratios (see Example 6). Subsequently, either the group of stress-resistant or the group of stress-prone subjects was exposed to a performance test followed by exposure to a stress. This stress consisted of an arithmetic task that had to be performed under noise stimulation. Subjects were led to believe that the presence or absence of the noise was depended on their performance in the test. In reality, the arithmetic tasks were manipulated in such a way that all subjects failed each trial. This set up is known to induce psychological stress and is perceived as highly uncontrolable (Peters, M. L., Godaert, G. L. R., Ballieux, R. E. et al. (1998). Cardiovascular and catecholamine response to experimental stress: effects of mental effort and controllability. Psychoneuroendocrinology. 23, 1-17). After the arithmatic task, the first performance test was repeated to quantify the effect of the stress on the performance under the influence of the blood Trp/LNAA ratios in force.

The performance tests carried out were the Mackworth Clock test (Mackworth, N (1948) The breakdown of vigilance during prolonged visual search. Quart J Exp Psych. 1, 6-21)) and the Critical Tracking Task (Jex H R et al., (1966) A "critical" tracking task for man-machine research related to the operator's effective delay time. NASA Contract Rep NASA CR.:1-105).

The Mackworth Clock Test is an extensively used test to measure "vigilance", alertness and concentration over a sustained period of time. Subjects are seated in front of a computer screen displaying a circular arrangement of 60 dots simulating the second marks on a clock. Dots are briefly illuminated in a clockwise rotation at a rate of one per 500 ms. Usually, the rotation proceeds with a single (one-dot) jump. Subjects were instructed that rarely, at irregular intervals, the target proceeds with a double (two-dot) jump by skipping one of the dots in the normal sequence. This should prompt the subjects to press a button as quickly as possible. A total of thirty such occasions were presented in the 45-minute test. Ten occasions occurred within each successive 15-minute period, with intervals ranging from 8 seconds to 7.2 minutes.

The Critical Tracking Task is used as a perceptual-motor performance task that measures the ability to control a displayed error signal in a first-order compensatory perceptual-motor coordination task. During this task, subjects have to control an unstable cursor on a computer screen by using a sensitive joystick. Errors will appear as horizontal deviations of the cursor from the midpoint on a horizontal linear scale. Subjects have to try to keep the unstable cursor in the center of the axis, to reduce deviations back to zero, by continuously making compensatory joystick movements. The frequency of cursor deviations increases as a stochastic, linear function of time, and therefore the subject is required to make compensatory movements with a progressively higher frequency. Also, the subject's compensatory responses increase in frequency with an increasing phase lag (a response adds to, rather than subtracts from, the error) and consequently control is lost. The frequency at which the subjects lose the control is the critical frequency. The test was performed five times; the average critical frequency was calculated without the lowest and highest score as the dependent variable of this test.

The plasma Trp/LNAA ratios determined 90 minutes after consumption of the drinks, revealed a significant effect ($P<0.0001$) on plasma Trp/LNAA ratio changes across the experimental conditions as applied. Ingestion of the lysozyme hydrolysate ("Trp-hydr") increased plasma Trp/LNAA value to 0.25 µmol/l. Ingestion of the casein hydrolysate ("plc") to a Trp/LNAA ratio of 0.08 µmol/l (FIG. 6) The values for each of the relevant amino acids are provided in Table 5.

TABLE 5

Amino acid concentrations (µmol/l) following ingestion of the placebo ("plc") or the lysozyme hydrolysate ("Trp-hydr").

| | Tyr | Val | Ile | Phe | Leu | Trp | LNAA | Trp/LNAA |
|---|---|---|---|---|---|---|---|---|
| plc | 90 | 315 | 107 | 63 | 168 | 60 | 744 | 0.082 |
| Trp-hydr | 73 | 266 | 120 | 58 | 152 | 167 | 670 | 0.250 |

After ingestion of the casein hydrolysate, the performance of both groups of individuals subjected to the Mackworth Clock Test was significantly impaired by exposure to stress. However, ingestion of the Trp-rich lysozyme hydrolysate prevented such an impaired performance in the stress-resistant group. Quite surprisingly, the Trp-rich hydrolysate did not prevent such an impaired performance in the stress-prone group. The data obtained are graphically represented in FIG. 7.

In the Critical Tracking Task, the lambda CT value indicates the final level of complexity that is reached by the subjects. The higher the lambda CT value, the better the control. The data obtained in the present experiment show that after exposure to stress, the lambda CT value was significantly higher when the Trp-rich hydrolysate was consumed. Among the stress-resistant individuals, a 16% increase could be scored relative to the placebo treatment. Quite surprisingly, also in this test, the lambda CT values in the stress-prone group showed no significant differences between the Trp-rich hydrolysate and the placebo.

The invention claimed is:

1. A method of improving: mood, cognition, sleep onset and quality, or depression in a subject in need thereof, or alertness or vigilance in a stress-resistant healthy subject in need thereof, said method comprising: administering to said subject a composition comprising at least two different water-soluble, tryptophan-containing peptides and wherein the Trp/large neutral amino acid (LNAA) ratio of the composition is at least 0.15; and wherein the composition is made by a process comprising:
   a) hydrolyzing hen egg lysozyme at an alkaline pH with a subtilisin to prepare a hydrolysate having a degree of hydrolysis (DH) of between 5 and 45; and
   b) removing part of the arginine or lysine containing peptides.

2. The method of claim 1, wherein the composition comprises at least one of AW or GNW.

3. A method of increasing the Trp/large neutral amino acid (LNAA) ratio in plasma within 90 minutes after uptake of peptides comprising administering to a subject in need thereof a composition comprising at least two different water-soluble, tryptophan-containing peptides and wherein the Trp/LNAA ratio of the composition is at least 0.15, and wherein the composition is made by a process comprising:
   a) hydrolyzing hen egg lysozyme at an alkaline pH with a subtilisin to prepare a hydrolysate having a degree of hydrolysis (DH) of between 5 and 45; and
   b) removing part of the arginine or lysine containing peptides.

4. The method of claim 3 further comprising uptake of protein or protein containing food at the same time or almost the same time as the administration of the composition.

5. The method of claim 3 wherein the Trp/LNAA ratio in plasma is higher than the Trp/LNAA ratio of the composition.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Artificial sequence
<220> FEATURE:
<223> OTHER INFORMATION: Description of Artificial Sequence: Synthesized

<400> SEQUENCE: 1

Ser Leu Gly Asn Trp
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthesized

<400> SEQUENCE: 2

Ser Arg Trp Trp
1